US011547679B2

(12) United States Patent
Lisanti et al.

(10) Patent No.: US 11,547,679 B2
(45) Date of Patent: *Jan. 10, 2023

(54) MITORIBOSCINS: MITOCHONDRIAL-BASED THERAPEUTICS TARGETING CANCER CELLS, BACTERIA AND PATHOGENIC YEAST

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 114 days.

This patent is subject to a terminal disclaimer.

(21) Appl. No.: 16/670,326

(22) Filed: Oct. 31, 2019

(65) Prior Publication Data

US 2020/0170967 A1 Jun. 4, 2020
US 2021/0186898 A9 Jun. 24, 2021

Related U.S. Application Data

(63) Continuation of application No. 16/204,173, filed on Nov. 29, 2018, now Pat. No. 10,512,618, which is a continuation of application No. PCT/US2018/022403, filed on Mar. 14, 2018.

(60) Provisional application No. 62/471,688, filed on Mar. 15, 2017.

(51) Int. Cl.

| A61K 31/55 | (2006.01) |
|---|---|
| C07D 403/04 | (2006.01) |
| A61P 31/00 | (2006.01) |
| A61P 35/00 | (2006.01) |
| A61K 31/137 | (2006.01) |
| C07D 295/135 | (2006.01) |
| C07C 217/74 | (2006.01) |
| C07D 223/04 | (2006.01) |
| C07D 401/04 | (2006.01) |
| C07C 235/46 | (2006.01) |
| C07D 491/107 | (2006.01) |
| C07C 275/24 | (2006.01) |
| C07D 513/04 | (2006.01) |
| C07D 207/06 | (2006.01) |
| A61P 15/16 | (2006.01) |
| A61K 31/14 | (2006.01) |
| A61K 31/155 | (2006.01) |
| A61K 31/66 | (2006.01) |
| G16C 20/50 | (2019.01) |
| A61K 9/00 | (2006.01) |
| A61K 31/40 | (2006.01) |
| A61K 31/436 | (2006.01) |
| A61K 31/519 | (2006.01) |
| A61K 31/5513 | (2006.01) |

(52) U.S. Cl.
CPC ............ *A61K 31/137* (2013.01); *A61K 31/14* (2013.01); *A61K 31/155* (2013.01); *A61K 31/66* (2013.01); *A61P 15/16* (2018.01); *A61P 31/00* (2018.01); *A61P 35/00* (2018.01); *C07C 217/74* (2013.01); *C07C 235/46* (2013.01); *C07C 275/24* (2013.01); *C07D 207/06* (2013.01); *C07D 223/04* (2013.01); *C07D 295/135* (2013.01); *C07D 401/04* (2013.01); *C07D 403/04* (2013.01); *C07D 491/107* (2013.01); *C07D 513/04* (2013.01); *A61K 9/0014* (2013.01); *A61K 31/40* (2013.01); *A61K 31/436* (2013.01); *A61K 31/519* (2013.01); *A61K 31/5513* (2013.01); *G16C 20/50* (2019.02)

(58) Field of Classification Search
None
See application file for complete search history.

(56) References Cited

U.S. PATENT DOCUMENTS

| 3,847,983 | A | 11/1974 | Kobayashi et al. | |
|---|---|---|---|---|
| 5,756,507 | A | 5/1998 | Goulet et al. | |
| 8,097,626 | B2* | 1/2012 | Busch-Petersen | A61P 25/28 |
| | | | | 544/336 |
| 2008/0058290 | A1 | 3/2008 | Reddy et al. | |
| 2008/0275053 | A1* | 11/2008 | Giblin | A61P 3/10 |
| | | | | 514/252.1 |
| 2011/0104162 | A1 | 5/2011 | Carniato et al. | |

(Continued)

FOREIGN PATENT DOCUMENTS

| CA | 2 884 607 A1 | 9/2016 |
|---|---|---|
| EP | 1 818 340 A1 | 8/2007 |
| WO | WO 2008/115381 A1 | 9/2008 |

OTHER PUBLICATIONS

Gellatly et al. "Pseudomonas aeruginosa: New Insights into Pathogenesis and Host Defenses". Pathogens and Disease. 2013; 67: 159-173. (Year: 2013).*

(Continued)

*Primary Examiner* — Leslie A. Royds Draper
(74) *Attorney, Agent, or Firm* — Nixon & Vanderhye, P.C.

(57) ABSTRACT

The present disclosure relates to inhibitors of mitochondrial function. Methods of screening compounds for mitochondrial inhibition are disclosed. Also described are methods of using mitochondrial inhibitors called mitoriboscins—mitochondrial-based therapeutic compounds having anti-cancer and antibiotic properties—to prevent or treat cancer, bacterial infections, and pathogenic yeast, as well as methods of using mitochondrial inhibitors to provide anti-aging benefits. Specific mitoriboscin compounds and groups of mitoriboscins are also disclosed.

3 Claims, 26 Drawing Sheets

(56) References Cited

U.S. PATENT DOCUMENTS

2014/0288077 A1     9/2014   Fujii et al.
2015/0361077 A1*   12/2015   Simpson .............. A61K 31/505
                                                                                  514/249

OTHER PUBLICATIONS

Rebecca Lamb, et al., "Antibiotics that target mitochondria effectively eradicate cancer stem cells, across multiple tumor types: Treating cancer like an infectious disease", Oncotarget, Jan. 22, 2015, pp. 4569-4584, vol. 6, No. 7.
Bela Ozsvari, et al., "Mitoriboscins: Mitochondrial-based therapeutics targeting cancer stem cells (CSCs), bacteria and pathogenic yeast", Oncotarget, Jul. 7, 2017, pp. 67457-67472, vol. 8, No. 40.
"2-Benzyloxyaniline", PubChem Open Chemistry Database, CID No. 240548, Mar. 26, 2005, 19 pages, <https://pubchem.ncbi.nlm.nih.gov/compound/240548>.
"USCWVRZHUKATDL-DNRSQYFGSA-N", PubChem Open Chemistry Database, CID No. 110135536, Jan. 18, 2016, 11 pages, <https:// pubchem.ncbi.nlm.nih.gov/compound/110135536>.
International Search Report and Written Opinion of the ISA for PCT/US2018/022403, dated Jul. 20, 2018, 11 pages.
Gilleron et al., "Identification of siRNA delivery enhancers by a chemical library screen," Nucleic Acids Research, vol. 43, No. 16, Jul. 28, 2015, pp. 7984-8001 (XP055547439).
Gilleron et al., "Supplementary Data to: Identification of siRNA delivery enhancers by a chemical library screen," Nucleic Acids Research, Jul. 28, 2015 (XP055547448).
Guo et al., "Synthesis and bioactivity of N, N'-Bis-substituted urea derivatives as novel small molecular inhibitors of cysteine protease of Trypanosoma cruzi," (XP002788354), Retrieved from STN, Database Accession No. 2004:912828 with Guo et al., "Synthesis and bioactivity of N, N'-Bis-substituted urea derivatives as novel small molecular inhibitors of cysteine protease of Trypanosoma cruzi," Zhongguo Yaoke Daxue Xuebao, 34(6) pp. 491-495, 2003 (XP009510743).
Ha et al., "Discovery of Novel CXCR2 Inhibitors Using Ligand-Based Pharmacophore Models," Journal of Chemical Information and Modeling, vol. 55, No. 8, Jul. 23, 2015, pp. 1720-1738 (XP055547587) with Ha et al., "Supplementary materials and methods to: Discovery of Novel CXCR2 Inhibitors Using Ligand-Based Pharmacophore Models,"Journal of Chemical Information and Modeling, vol. 55, No. 8, Aug. 24, 2015, pp. 1720-1738 (XP055547978).
Mani et al., "Probing Binding and Cellular Activity of Pyrrolidinone and Piperidinone Small Molecules Targeting the Urokinase Receptor," CHEMMEDCHEM, vol. 8, No. 12, Dec. 2, 2013, pp. 1963-1977 (XP55386919).
Ohta et al., "Novel 5-Hydroxytryptan1ine (5-HT$_3$) Receptor Antagonists. II.[1)] Synthesis and Structure-Activity Relationships of 4,5,6,7-Tetrahydro-1H-benzimidazole Derivatives,"Jan. 1, 1996, pp. 1000-1008 (XP055547596).
Ottosson et al., "Potent Inducers of Endogenous Antimicrobial Peptides for Host Directed Therapy of Infections," Scientific Reports, vol. 6, No. 1, Nov. 9, 2016, (XP055547477).
Database Registry [Online], Chemical Abstracts Service, Jan. 26, 2017 (XP002788355), Retrieved from STN, Database Accession No. 2059764-23-5.
Database Registry [Online], Chemical Abstracts Service, Jan. 25, 2017 (XP002788356), Retrieved from STN, Database Accession No. 2058655-99-3.
Database Registry [Online], Chemical Abstracts Service, Jan. 31, 2017 (XP002788357), Retrieved from STN, Database Accession No. 2062025-32-3.
Database Registry [Online], Chemical Abstracts Service, Sep. 14, 2017 (XP002788358), Retrieved from STN, Database Accession No. 2127176-25-2.
Database Registry [Online], Chemical Abstracts Service, Oct. 13, 2017 (XP002788359), Retrieved from STN, Database Accession No. 2134616-41-2.
Database Registry [Online], Chemical Abstracts Service, Sep. 17, 2017 (XP002788360), Retrieved from STN, Database Accession No. 2128079-22-9.
Database Registry [Online], Chemical Abstracts Service, Sep. 14, 2017 (XP002788361), Retrieved from STN, Database Accession No. 2127204-21-9.
Aurora Fine Chemicals [Online]. "Customer Support". [Retrieved Apr. 13, 2019]. Retrieved from the Internet: <URL: https://www.aurorafinechennicals.conn/custonner-support.htnnl>. Three Pages.
Google Indexing for Aurora Fine Chemicals. "Customer Support". Availability Date of Jan. 27, 2017.
Ozsvari et al. "Mitoriboscins: Mitochondrial-Based Therapeutics Targeting Cancer Stem Cells (CSCs), Bacteria and Pathogenic Yeast". Jul. 7, 2017; 8(40):67457-67472. (Year: 2017).
Holliday et al. "Choosing the Right Cell Line for Breast Cancer Research". Breast Cancer Research. 2011; 13:215. (Year: 2011).
Pelicano et al. "Glycolysis Inhibition for Anticancer Treatment". Oncogene. 2006; 25:4633-4646. (Year: 2006).
Golding et al. "Targeting Tumour Energy Metabolism Potentiates the Cytotoxicity of 5-Aminolevulinic Acid Photodynamic Therapy". British Journal of Cancer. 2013; 109:976-982. (Year: 2013).
PubChem., "3-(4-Fluorophenyl)-7-piperidin-1-yl-[1,2] thiazolo [4,5-d]pyrimidine"—SID 43814242.-2009.-C.1.—Jul. 21, 2009.

* cited by examiner

```
                Virtual high-throughput screening (vHTS)
                              For example:
S101         Selection of a library of 880 compounds
                 (from a small molecule screening
                  collection of 45,000 compounds)
          'Cherry picking' based on the 3-D molecular structure
          of the large subunit (39S) of the mammalian mitoribosome
```

Phenotypic drug screening
                                    For example:
                                  ATP-depletion assays
S103                           on human breast cancer cells
                                       (MCF7)
                             Tested 880 compounds at 50 µM
                                Observed 30 hits at 25 µM
                                Observed 10 hits at 10 µM Functional validation
                                    For example:
S105                          Metabolic Flux analysis
                               Mammosphere assays
                                  Viability assays
                             Anti-Bacterial/Fungal Activity

FIG. 2

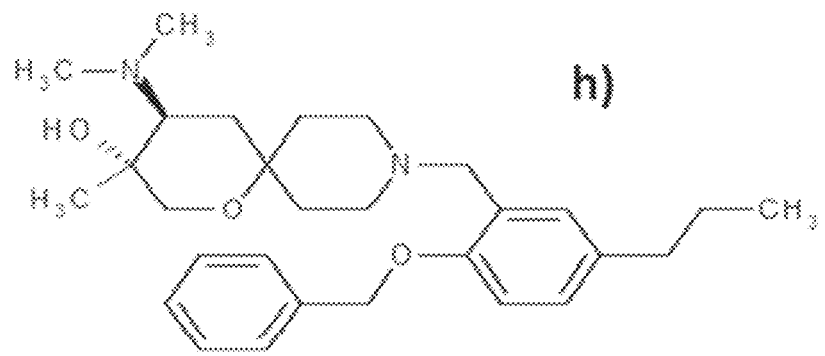
h)
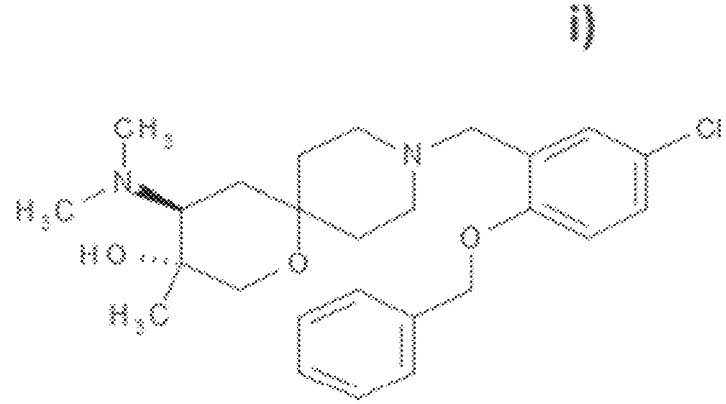
i)
FIG. 4C

MITORIBOSCIN GROUPS
Mitoribocyclines
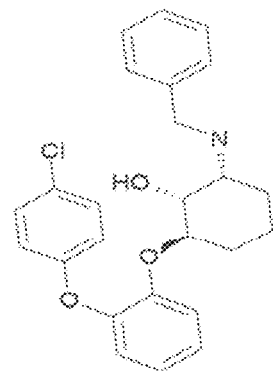
Mitoribomycins
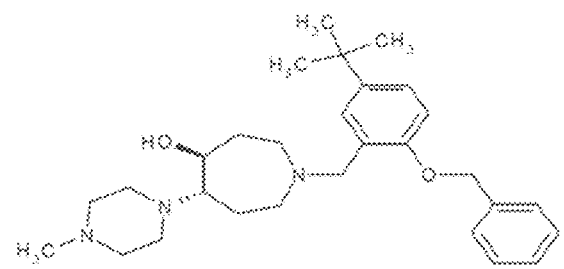
Mitoribosporins
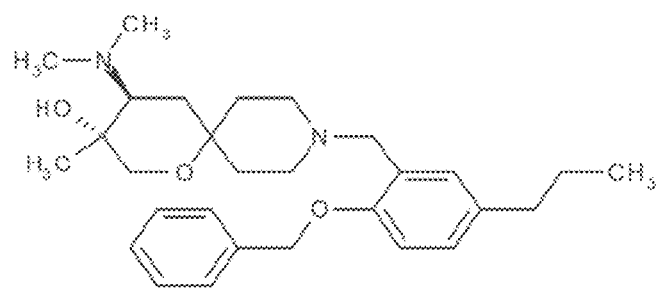
Mitoribofloxins
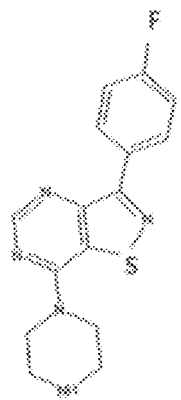
FIG. 12

MITORIBOSCINS: MITOCHONDRIAL-BASED THERAPEUTICS TARGETING CANCER CELLS, BACTERIA AND PATHOGENIC YEAST

CROSS-REFERENCE TO RELATED APPLICATIONS

This application is a Continuation of U.S. patent application Ser. No. 16/204,173 filed Mar. 14, 2018, which is a Continuation of International Application No. PCT/US2018/022403 filed Mar. 14, 2018, which claims the benefit of U.S. Provisional Patent Application No. 62/471,688, filed Mar. 15, 2017, the entirety of each of which are incorporated herein by reference.

FIELD

The present disclosure relates to novel inhibitors of mitochondrial function that target the mitochondrial ribosome, referred to herein as "mitoriboscins," methods for identifying mitoriboscins, methods of using the inhibitors to target cancer stem cells, to target bacteria and pathogenic yeast, and to provide anti-aging benefits, and pharmaceutical compositions for treating cancer, bacterial infections, yeast infections, and aging, containing one or more mitoriboscins as the active ingredient.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed. Similarly, researchers have struggled to develop new antibiotic treatments. Antibiotic resistance has developed due to gradual buildup of random mutations in the microbes and the misuse of antibiotics. Poor financial investment in antibiotic research and development has worsened the situation. Hence, novel antibiotic treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle*, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget*, 5(22):11029-11037 (2014). Functional inhibition of mitochondrial biogenesis using the off-target effects of certain bacteriostatic antibiotics or OXPHOS inhibitors provides additional evidence that functional mitochondria are required for the propagation of cancer stem cells.

There exists a need in the art for novel anticancer strategies, new compounds with broad-spectrum antibiotic activity, and compounds to reduce the effects of aging. The "endo-symbiotic theory of mitochondrial evolution" can be used as the basis for the development of therapies to treat drug-resistance that is characteristic of both tumor recurrence and infectious disease, and such therapies may have the additional benefit of slowing the aging process.

SUMMARY

In view of the foregoing background, it is therefore an object of this disclosure to demonstrate that mitochondrial biogenesis plays a critical role in the propagation and maintenance of many cancers. It is also an object of this disclosure to present methods for identifying mitochondrial inhibitors that bind to the mitochondrial ribosome (large sub-unit or small sub-unit) and have anti-cancer and antibiotic properties. It is also an object of this disclosure to identify mitochondrial inhibitors and groups thereof and having anti-cancer and antibiotic properties. It is also an object of this disclosure to identify classes of mitochondrial inhibitors having anti-aging properties. It is also an object of this disclosure to identify classes of mitochondrial inhibitors that function as radiosensitizers and photosensitizers.

The present disclosure relates to mitochondrial inhibitor compounds that have anti-cancer and antimicrobial activity, radiosensitizing and photosensitizing effects, as well as anti-aging effects. The term "mitoriboscins" broadly refers to mitoribosome-targeted therapeutics having anti-cancer and antibiotic properties. These compounds bind to either the large sub-unit or the small sub-unit of the mitoribosome (or in some instances, both) and inhibit mitochondrial biogenesis. The present disclosure further relates to methods of identifying mitoriboscins, methods of making such mitoriboscins, and methods of using mitoriboscins for therapeutic purposes.

The inventors analyzed phenotypic properties of cancer stem cells (CSCs) that could be targeted across a wide range of cancer types, and identified a strict dependence of CSCs on mitochondrial biogenesis for the clonal expansion and survival of a CSC. Previous work by the inventors demonstrated that different classes of FDA-approved antibiotics, and in particular tetracyclines such as doxycycline and erythromycin, have an off-target effect of inhibiting mitochondrial biogenesis. As a result, such compounds could have efficacy for eradicating CSCs. However, these common antibiotics were not designed to target the mitoribosome, and therefore have limited anti-cancer properties. Under the present approach, the inventors have identified compounds that target the mitochondrial ribosome, or mitoribosome, and inhibit mitochondrial biogenesis. These mitoribosome-targeting compounds—mitoriboscins—therefore have highly potent anticancer properties, among other advantageous properties.

Given the role of mitochondrial biogenesis in cell propagation, mitochondrial inhibitors as identified under the present approach provide an entirely new class of cancer therapy. In addition to their potential use as cancer therapies, mitoriboscins serve as useful broad-spectrum antibiotics. The endo-symbiotic theory of mitochondrial evolution theorizes that mitochondrial organelles evolved from engulfed aerobic bacteria following millions of years of symbiosis and adaptation. The evolutionary history of mitochondrial organelles suggests that compounds that target mitochondrial protein translation in cancer cells also possess anti-microbial activity. Indeed, as discussed below, mitoriboscins have demonstrated antibiotic properties.

Additionally, studies on genetic inhibition of mitochondrial protein translation have shown beneficial "side effects," such as the slowing of the aging process and increased lifespan in model organisms. These results suggest that mitochondrial inhibitors may also be useful for anti-aging therapies, which is the subject of ongoing studies.

Novel mitochondrial inhibitors may be identified through a convergent approach of virtual high-throughput in silico screening followed by in vitro validation for mitochondrial inhibition. New mitochondrial inhibitors can be rapidly developed by combining in silico drug design with phenotypic drug screening.

BRIEF DESCRIPTION OF THE DRAWINGS

FIG. 2 shows a schematic diagram outlining a drug discovery strategy according to embodiments of the present approach.

FIGS. 4A-4D illustrates the chemical structures of ten mitoriboscin compounds identified following phenotypic drug screening. These structures are grouped into four groups—(1) mitoribocyclines (compounds a-c on FIG. 4A), (2) mitoribomycins (compounds d-g on FIG. 4B), (3) mitoribosporins (compound h and i on FIG. 4C), and (4) mitoribofloxins compound j on FIG. 4D).

FIG. 12 illustrates the four new classes of mitochondrial inhibitors—mitoribocyclines, mitoribomycins, mitoribosporins, and mitoribofloxins.

DESCRIPTION

Figure 1:
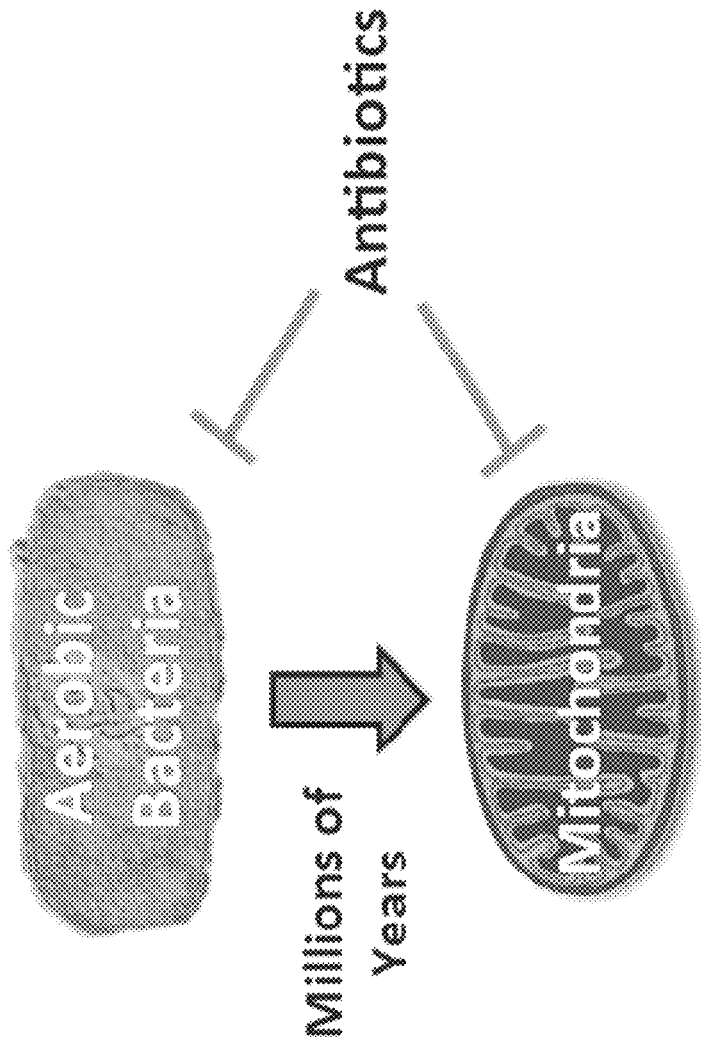
FIG. 1 illustrates the endo-symbiotic theory of mitochondrial evolution.

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The mitochondrial ribosome is an untapped gateway for treating a number of afflictions, ranging from cancer to bacterial and fungal infections to aging. Functional mitochondria are required for the propagation of cancer stem cells. Inhibiting mitochondrial biogenesis in cancer cells impedes the propagation of those cells. Mitochondrial inhibitors therefore represent a new class of anti-cancer therapeutics. These compounds may also inhibit mitochondrial protein translation, and therefore possess anti-microbial activity. As a result, mitochondrial inhibitors may function as broad-spectrum antibiotics that target both bacteria and pathogenic yeast. Research has also showed that mitochondrial inhibitors have anti-aging properties. This disclosure uses the term "mitoriboscins" to broadly describe these mitochondrial-based therapeutic compounds having anti-cancer and antibiotic properties. Mitoriboscins at lower doses may be used to therapeutically target the aging process and to extend lifespan.

Novel mitochondrial inhibitors that target the mitoribosome—mitoriboscins—may be identified through a convergent approach of virtual high-throughput screening followed by in vivo validation for mitochondrial inhibition. FIG. 2 is an overview of methods for identifying mitochondrial inhibitors by using in silico drug screening and phenotypic drug screening disclosed herein. All or a portion of the three-dimensional structure of the mammalian mitochondrial ribosome (mitoribosome) may be used in step S101 to identify novel compounds that bind to the mitoribosome through virtual high-throughput screening (vHTS) (i.e., in silico drug screening). The screening may be performed across a library of molecules. For instance, during initial investigations the inventors screened a collection of 45,000 small molecule compounds for compounds expected to bind anywhere to the known large subunit of the large mitoribosome (39S), which is a multi-subunit complex with more than 50 subunits. Initial vHTS may use various screening programs, such as the eHiTS screening program, to identify a subset of compounds having a strong binding affinity to either the large or small subunit of the mammalian mitoribosome. For example, the inventors used eHiTS to identify the top 5,000 ranked compounds from an initial library, based on predicted binding affinity to the large subunit (39S) of the mammalian mitoribosome. eHiTS is a screening method that systematically covers the part of the conformational and positional search space that avoids severe steric clashes, producing highly accurate docking poses at a speed that is well-suited for virtual high-throughput screening.

It should be appreciated that those skilled in the art may select or develop methods for identifying a subset of compounds having a desired binding affinity. To efficiently perform the docking, a series of clip files may be prepared corresponding to the entire protein structure and each compound docked sequentially at each of the clip files. Consensus scoring of the top compounds may be carried out using AutoDock 4.2, based on the same general binding site for each compound predicted from the eHiTS screen. Further analysis of predicted binding affinity and visual inspection may be carried out using a number of methods, including for example a de novo design program such as SPROUT. See Law et al., *J Mol Struct*. 666: 651-657 (2003), which is incorporated by reference in its entirety, for information about SPROUT. Depending on the initial library size and results, a number of compounds may be selected for phenotypic drug screening. For example, the inventors selected 880 compounds that performed well in these analysis steps for phenotypic drug screening at step S103.

Figure 3:
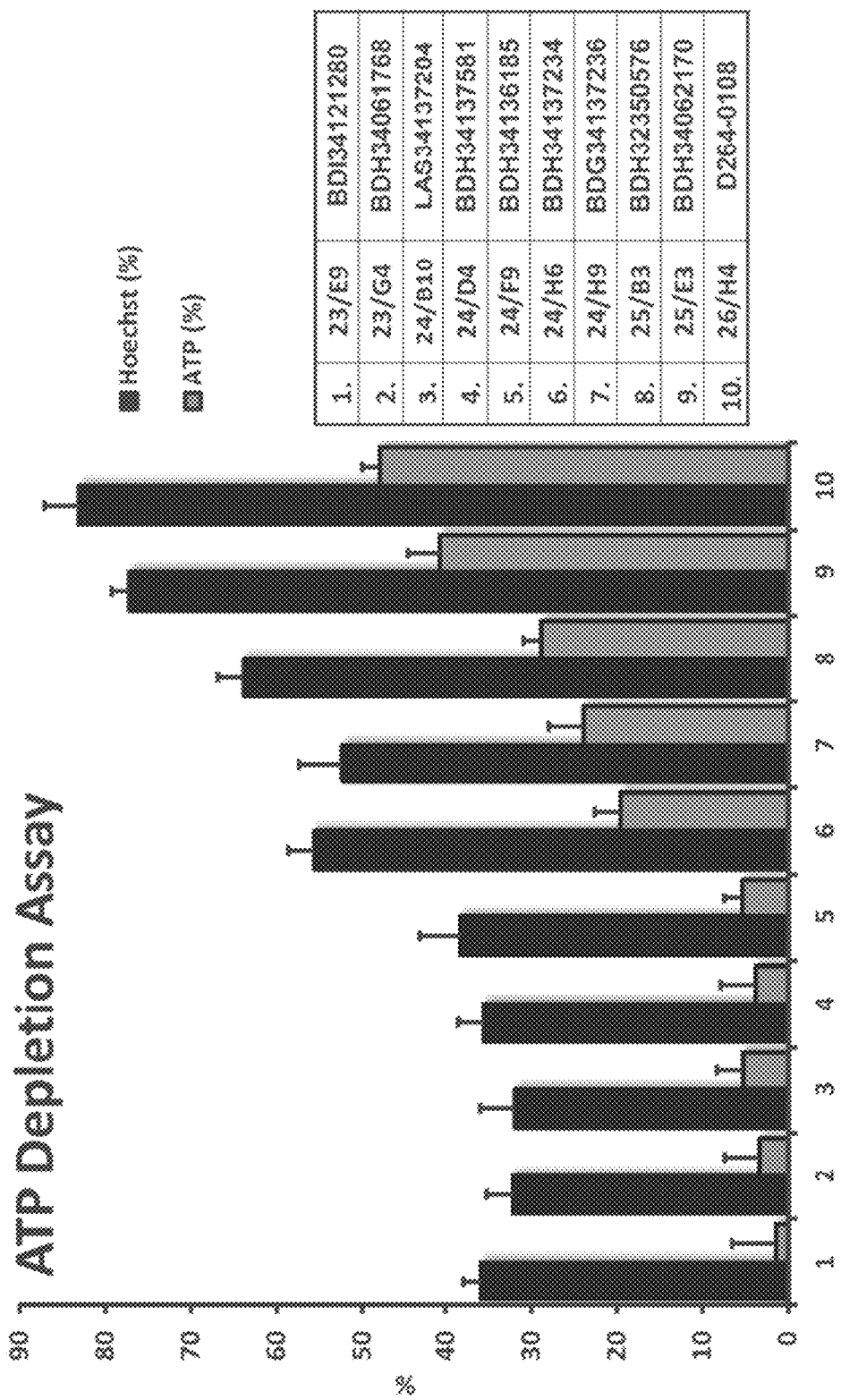
FIG. 3 shows the effects of ten candidate mitoriboscin compounds on ATP-depletion in MCF7 cells.

Phenotypic drug screening S103 may be accomplished by testing the mitochondrial inhibition of selected compounds in a selected cell line. For example, ATP depletion assays may be used. The inventors tested the selected 880 compounds on their ability to functionally induce ATP-depletion in MCF7 human breast cancer cells. Approximately 85% of cellular ATP is normally generated by OXPHOS in mitochondria, so ATP-depletion is a surrogate marker for mitochondrial inhibition. It should be appreciated that those skilled in the art may employ other surrogates for mitochondrial inhibition. However, for the ATP-depletion assay inventors employed, MCF7 cells (6,000 cells/well) were plated into black clear-bottom 96-well plates and incubated overnight before treatment. The 880 compounds identified by vHTS were applied to the plated MCF7 cells at a concentration of 50 μM and were screened for ATP depletion. Compounds showing ATP-depletion effects were subsequently re-screened at lower concentrations (25 μM and 10 μM) to identify the top 10 compounds that most potently induce ATP-depletion. Compounds were tested after 72 hours of incubation and experiments were performed in duplicate. After treatment, media was aspirated from the wells and plates were washed with warm phosphate-buffered saline (PBS) supplemented with $Ca^{2+}$ and $Mg^{2+}$. Then, cells were incubated with a Hoechst 33342 (Sigma) staining solution (10 μg/ml) for 30 min and washed with PBS to estimate cell viability. Fluorescence was read with a plate reader using excitation/emission wavelengths at 355/460-nm. Then, the CellTiter-Glo luminescent assay (Promega) was performed to measure metabolic activity (ATP content) in the very same wells that were treated with a given compound. Assays were performed according to the manufacturer's protocol. Fluorescence intensity (Hoechst staining) and luminescence intensity (ATP content) were normalized to vehicle-alone treated controls and were displayed as percent control for comparison. The results of this ATP depletion study are shown in FIG. 3. FIG. 3 shows that all ten test compounds significantly depleted ATP levels in viable cells. It should be appreciated that those of skill in the art may choose to employ the same or similar ATP-depletion assays, modify such assays, or may replace the ATP-depletion assay with another methodology for screening selected compounds for mitochondrial inhibition (e.g., oxygen consumption assays).

The present approach includes methods of confirming cell viability. Persons of skill in the art may select one or more methods for confirming cell viability suitable for the particular embodiment. The inventors initially used the Sulphorhodamine (SRB) assay, which is based on the measurement of cellular protein content. After treatment for 72 hours in 96-well plates, cells were fixed with 10% trichloroacetic acid (TCA) for 1 hour in the cold room, and were dried overnight at room temperature. Then, cells were incubated with SRB for 15 min, washed twice with 1% acetic acid, and air dried for at least 1 hour. Finally, the protein-bound dye was dissolved in a 10 mM Tris, pH 8.8 solution and read using the plate reader at 540-nm. Using the SRB assay, the inventors selected only the compounds depleting ATP levels without prominent cytotoxicity for further analysis. Prominent cytotoxicity was defined as fewer than 30% of cells still on the plate. Of course, embodiments employing other cell viability confirmation methodology may select compounds for further analysis based on other considerations as may be known in the art.

The present approach further involves methods of functional validation at step S105, during which a compound's function as a mitochondrial inhibitor may be confirmed. A number of methods may be used for functional validation, including, for example, metabolic flux analysis, mammosphere assays, viability assays, and antibiotic (anti-bacterial and/or anti-fungal) activity. For example, the inventors determined extracellular acidification rates (ECAR) and real-time oxygen consumption rates (OCR) for MCF7 cells using the Seahorse Extracellular Flux (XF96) analyzer (Seahorse Bioscience, MA, USA). MCF7 cells were maintained in DMEM supplemented with 10% FBS (fetal bovine serum), 2 mM GlutaMAX, and 1% Pen-Strep. 5,000 cells per well were seeded into XF96-well cell culture plates, and incubated overnight at 37° C. in a 5% $CO_2$ humidified atmosphere. After 24 hours, cells were treated with selected compounds showing ATP-depletion without prominent cytotoxicity at various concentrations (or vehicle alone). After 72 hours of treatment, cells were washed in pre-warmed XF assay media (for OCR measurement, XF assay media was supplemented with 10 mM glucose, 1 mM Pyruvate, 2 mM L-glutamine and adjusted at pH 7.4). Cells were maintained in 175 μL/well of XF assay media at 37° C. in a non-$CO_2$ incubator for 1 hour. During incubation, 25 μL of 80 mM glucose, 9 μM oligomycin, 1M 2-deoxyglucose (for ECAR measurement) and 25 μL of 10 μM oligomycin, 9 μM FCCP, 10 μM rotenone, 10 μM antimycin A (for OCR measurement) in XF assay media was loaded into the injection ports of the XFe-96 sensor cartridge. During the experiment, the instrument injected these inhibitors into the wells at a given time point, while ECAR/OCR was measured continuously. ECAR and OCR measurements were normalized by protein content (using the Sulphorhodamine B assay). Data sets were analyzed by XFe-96 software, using one-way ANOVA and Student's t-test calculations. All experiments were performed in triplicate, and results validated the mitochondrial inhibition effects of mitoriboscin compounds described herein. It should be appreciated that numerous methods are known for functional validation, and that persons of skill in the art may select one or more depending on the validation needs (e.g., other assays that measure or approximate mitochondrial function).

In summary, the present approach provides methods of identifying potential mitochondrial inhibitors and mitoriboscins using in silico drug screening and phenotypic drug screening. Novel compounds identified using this methodology may be tested for anti-cancer activity (e.g., the ability to inhibit mammosphere formation and cell migration) and may be further tested on distinct bacterial and/or yeast strains to investigate anti-microbial activity. FIG. 2 summarizes the general methods according to embodiments of the present approach, but it should be appreciated that those of skill in the art may deviate from the specific examples disclosed herein without departing from the present approach.

Figure 4A:
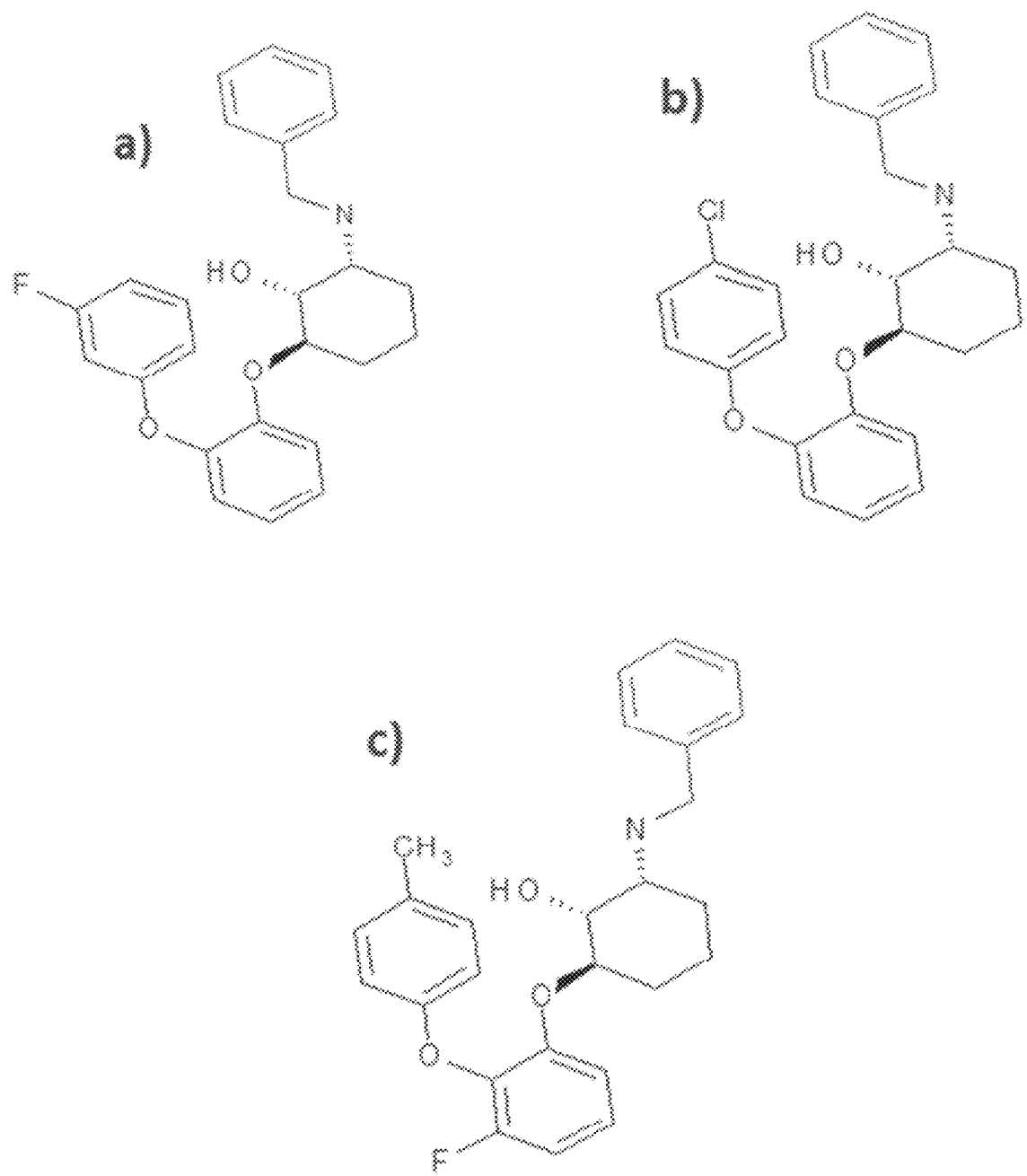
Figure 4B:
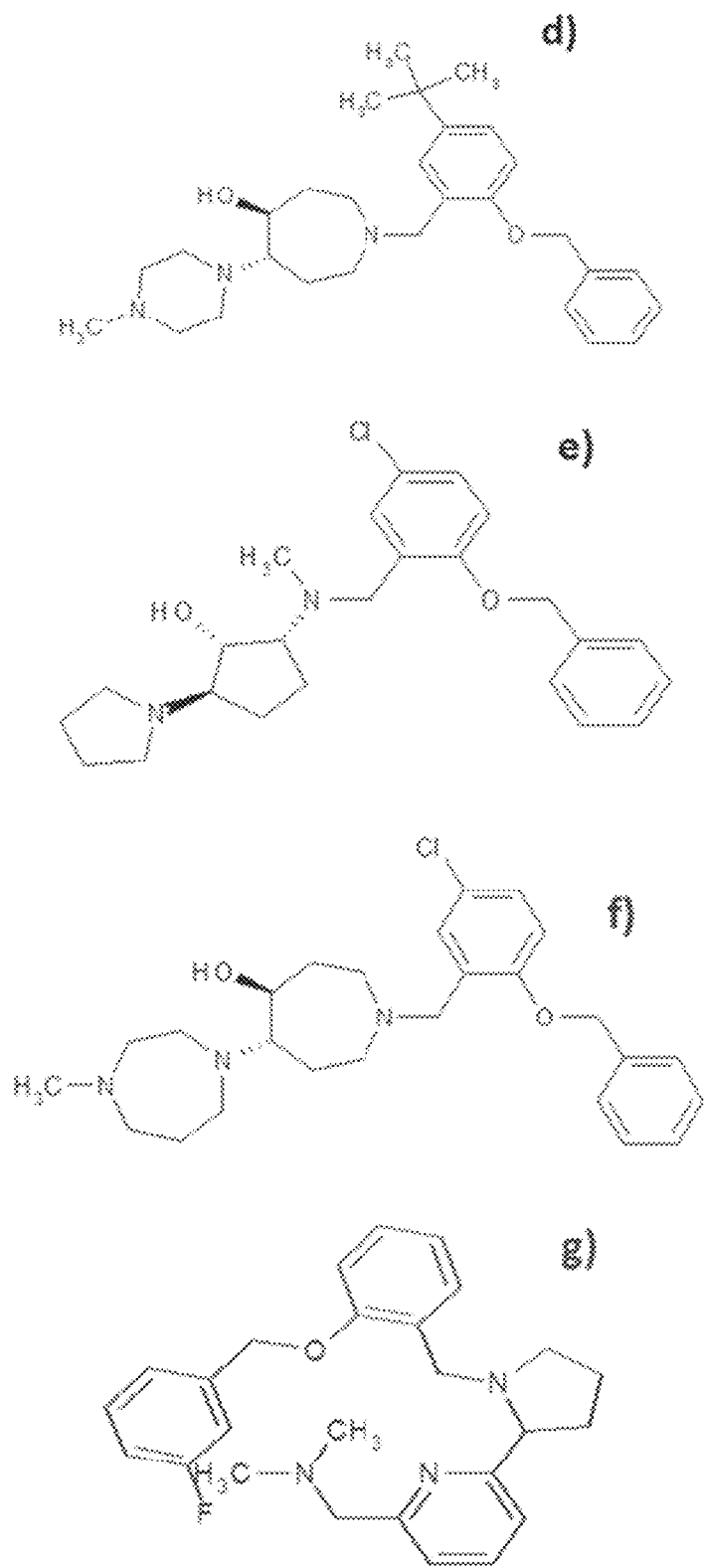
Figure 4D:
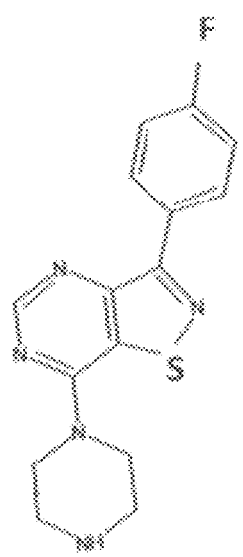

The present approach has led to the identification of categories of mitochondrial-inhibiting compounds—and in particular mitoriboscins—that have anti-cancer, anti-microbial, and anti-aging properties. Based on the inventors' initial screening and validation, the compounds identified in FIGS. 4A-D, have anti-cancer, anti-microbial, and anti-aging properties. The Group 1 compounds shown in FIG. 4A are mitoribocyclines, and include compounds a) 23/E9, b) 23/G4, and c) 25/E3. The Group 2 compounds shown in FIG. 4B are mitoribomycins, and include compounds d) 24/F9, e) 24/B10, f) 24/H6, and g) 25/B3. The Group 3 compounds shown in FIG. 4C are mitoribosporins, and include compounds h) 24/D4 and i) 24/H9. Finally, compound j) 26/H4, shown in FIG. 4D, is a mitoribofloxin. These unique mitoriboscins are therefore candidates for clinical trial. It should be appreciated that the mitoriboscins identified in FIG. 4 are not exhaustive, but are merely those that have been identified thus far using the novel methodology set forth herein.

The four mitoriboscin groups shown in FIGS. 4A-4D and 12, mitoribocyclines, mitoribomycins, mitoribosporins, and mitoribofloxins, may be selected for use as anti-cancer, antibiotic, and/or anti-aging therapeutics. It should be appreciated by those skilled in the art that the therapeutically-effective amount of each compound, for a particular therapy, depends on a multitude of factors. In some embodiments, combinations of compounds from one or more mitoriboscin groups may be used as anti-cancer, antibiotic, and/or anti-aging therapeutics.

In some embodiments, the mitoriboscin compound may be a mitoribocycline that comprises the general formula or salts thereof:

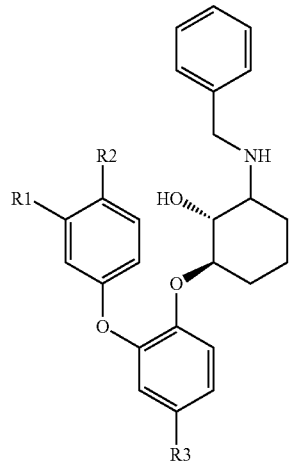

wherein each of R1-R3 may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and one or more mitochondrial targeting signals. As used herein, the term "derivative" is a chemical moiety derived or synthesized from a referenced chemical moiety. For clarification, mitochondrial targeting signals are defined as any chemical or peptide entity that increases the efficiency of targeting the attached molecule to the mitochondria. Such modification would be expected to increase the potency and effectiveness of a mitoriboscin. Thus, R may be any mitochondrial targeting signal (peptide or chemical), including cationic compounds, such as tri-phenyl-phosphonium (TPP), a guanidinium-based moiety and/or choline esters, among others.

In some embodiments, the mitoriboscin compound may be a mitoribomycin that comprises the general formula or salts thereof:

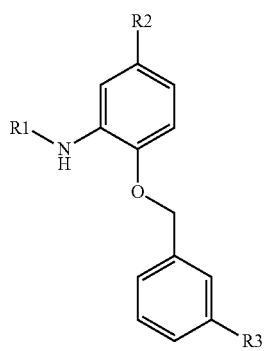

wherein each of R1-R3 may be the same or different and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and one or more mitochondrial targeting signals.

In some embodiments, the mitoriboscin compound may be a mitoribosporin that comprises the general formula or salts thereof:

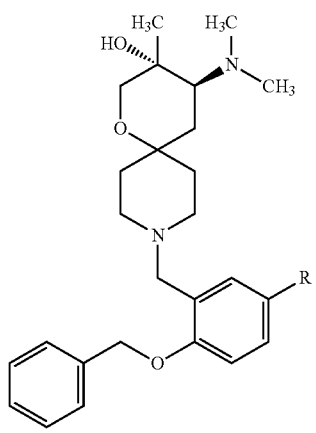

wherein R is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amine-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and one or more mitochondrial targeting signals.

In some embodiments, the mitoriboscin compound may be a mitoribofloxin that comprises the general formula or salts thereof:

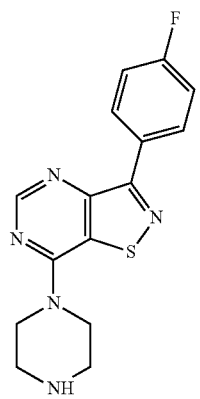

The specific mitoriboscins of the formulas shown in FIGS. 4A-4D are shown as specific examples of the groups of mitoriboscins identified in FIG. 12. It should be appreciated that the mitoriboscins may be selected for therapeutic use individually, or in combination with more than one specific mitoriboscin, and/or with other substances to enhance the efficacy of other therapeutics. The therapeutics may be used in the form of usual pharmaceutical compositions which may be prepared using one or more known methods. For example, a pharmaceutical composition may be prepared by using diluents or excipients such as, for example, one or more fillers, bulking agents, binders, wetting agents, disintegrating agents, surface active agents, lubricants, and the like as are known in the art. Various types of administration unit forms can be selected depending on the therapeutic purpose(s). Examples of forms for pharmaceutical compositions include, but are not limited to, tablets, pills, powders, liquids, suspensions, emulsions, granules, capsules, suppositories, injection preparations (solutions and suspensions), topical creams, and other forms as may be known in the art. For the purpose of shaping a pharmaceutical composition in the form of tablets, any excipients which are known may be used, for example carriers such as lactose, white sugar, sodium chloride, glucose, urea, starch, calcium carbonate, kaolin, cyclodextrins, crystalline cellulose, silicic acid and the like; binders such as water, ethanol, propanol, simple syrup, glucose solutions, starch solutions, gelatin solutions, carboxymethyl cellulose, shelac, methyl cellulose, potassium phosphate, polyvinylpyrrolidone, etc. Additionally, disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, etc., may be used. Disintegration inhibitors such as white sugar, stearin, coconut butter, hydrogenated oils; absorption accelerators such as quaternary ammonium base, sodium laurylsulfate, etc., may be used. Wetting agents such as glycerin, starch, and others known in the art may be used. Adsorbing agents such as, for example, starch, lactose, kaolin, bentonite, colloidal silicic acid, etc., may be used. Lubricants such as purified talc, stearates, boric acid powder, polyethylene glycol, etc., may be used. If tablets are desired, they can be further coated with the usual coating materials to make the tablets as sugar coated tablets, gelatin film coated tablets, tablets coated with enteric coatings, tablets coated with films, double layered tablets and multi-layered tablets. Pharmaceutical compositions adapted for topical administration may be formulated as ointments, creams, suspensions, lotions, powders, solutions, pastes, gels, foams, sprays, aerosols, or oils. Such pharmaceutical compositions may include conventional additives which include, but are not limited to, preservatives, solvents to assist drug penetration, co-solvents, emollients, propellants, viscosity modifying agents (gelling agents), surfactants and carriers.

Figure 5:
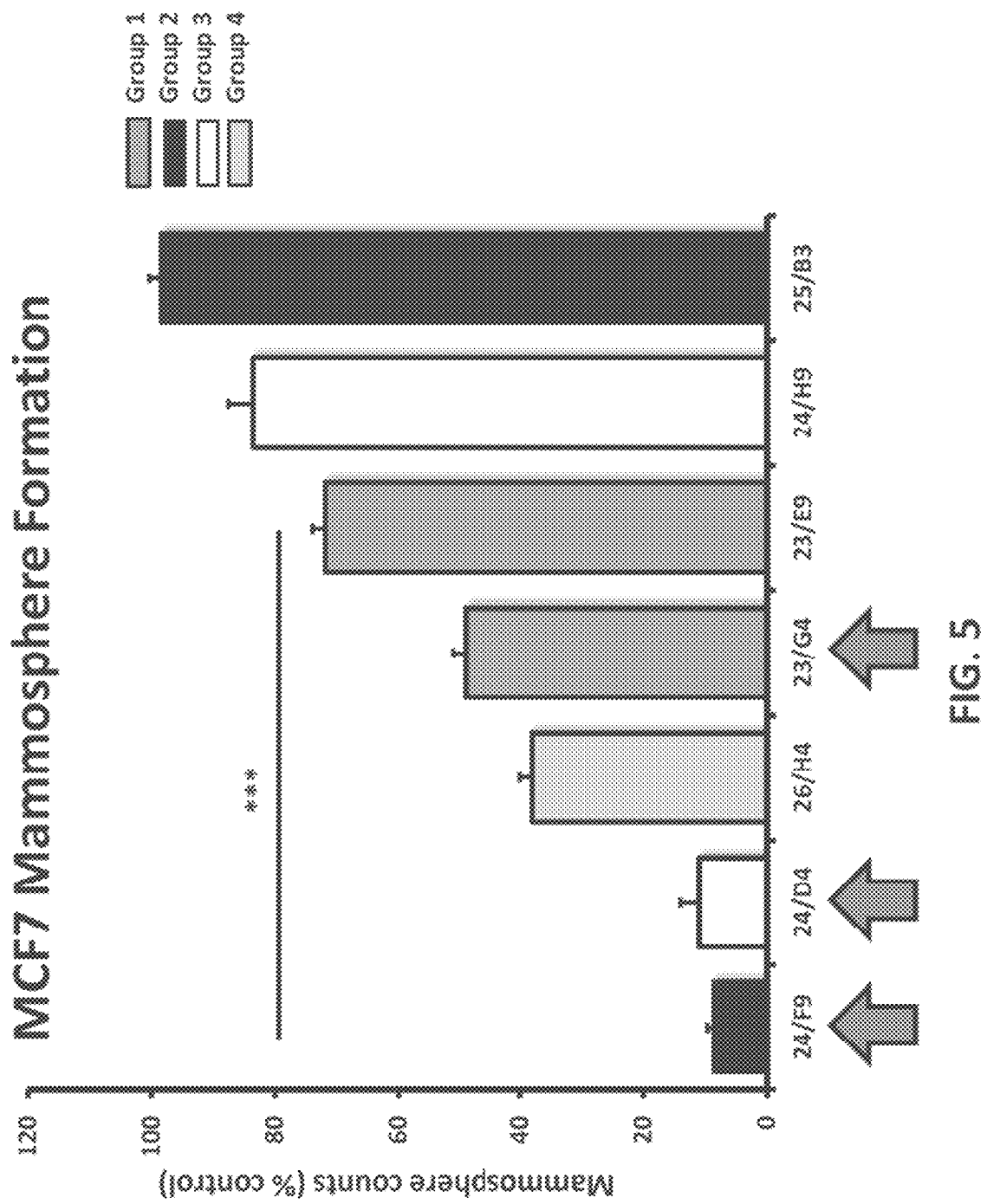
FIG. 5 shows the effects of seven mitoriboscin compounds on mammosphere formation in MCF7 cells.

The present approach involves methods of testing compounds, and in particular mitoriboscins, for anti-cancer properties. As discussed above, vHTS and computational chemistry may be used to identify candidate mitochondrial inhibitors. Those candidates may be tested for specific anti-cancer properties. For examples, the inventors compared seven candidate compounds in parallel for their ability to inhibit mammosphere formation in MCF7 cells. FIG. 5 illustrates how five of the seven compounds tested significantly inhibited mammosphere formation at a concentration of 5 µM. For example, 23/G4 (Group 1) reduced mammosphere formation by 50% at this concentration. Similarly, 24/F9 (Group 2) and 24/D4 (Group 3), both reduced mammosphere formation by ~90%.

Based on this analysis, the inventors assessed the functional effects of the three candidates on overall viability in MCF7 cell monolayers and normal human fibroblasts (hTERT-BJ1 cells) (FIG. 6). 23/G4 (Group 1) reduced the viability of MCF7 cells by 70% at a concentration of 5 µM. However, 23/G4 had no effect on the viability of hTERT-BJ1 cells, when tested at the same concentration. Thus, it is possible to identify compounds, such as 23/G4, that preferentially target CSCs and "bulk" cancer cells, but not normal fibroblasts. Those of skill in the art may determine the preferential targeting of candidate mitoriboscins employing the same method or other methods known in the art.

The present approach involves methods of function validation of mitoriboscin compounds. For example, the inventors assessed functional validation of three candidates using the Seahorse Analyzer, which quantitatively measures oxygen consumption rate (OCR) and extracellular acidification rate (ECAR). OCR is a surrogate marker for OXPHOS and ECAR is a surrogate marker for glycolysis and L-lactate production.

Figure 6A:
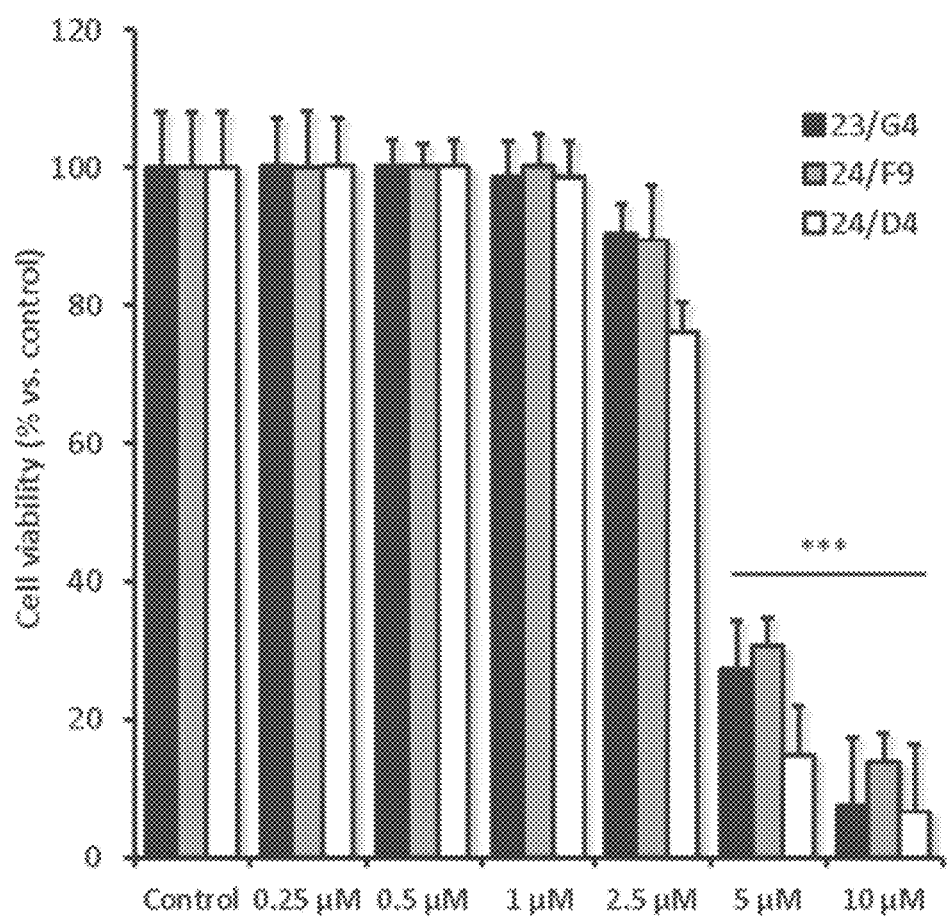
FIG. 6A shows the effects of three mitoriboscin compounds on the cell viability of MCF7 cells.
Figure 6B:
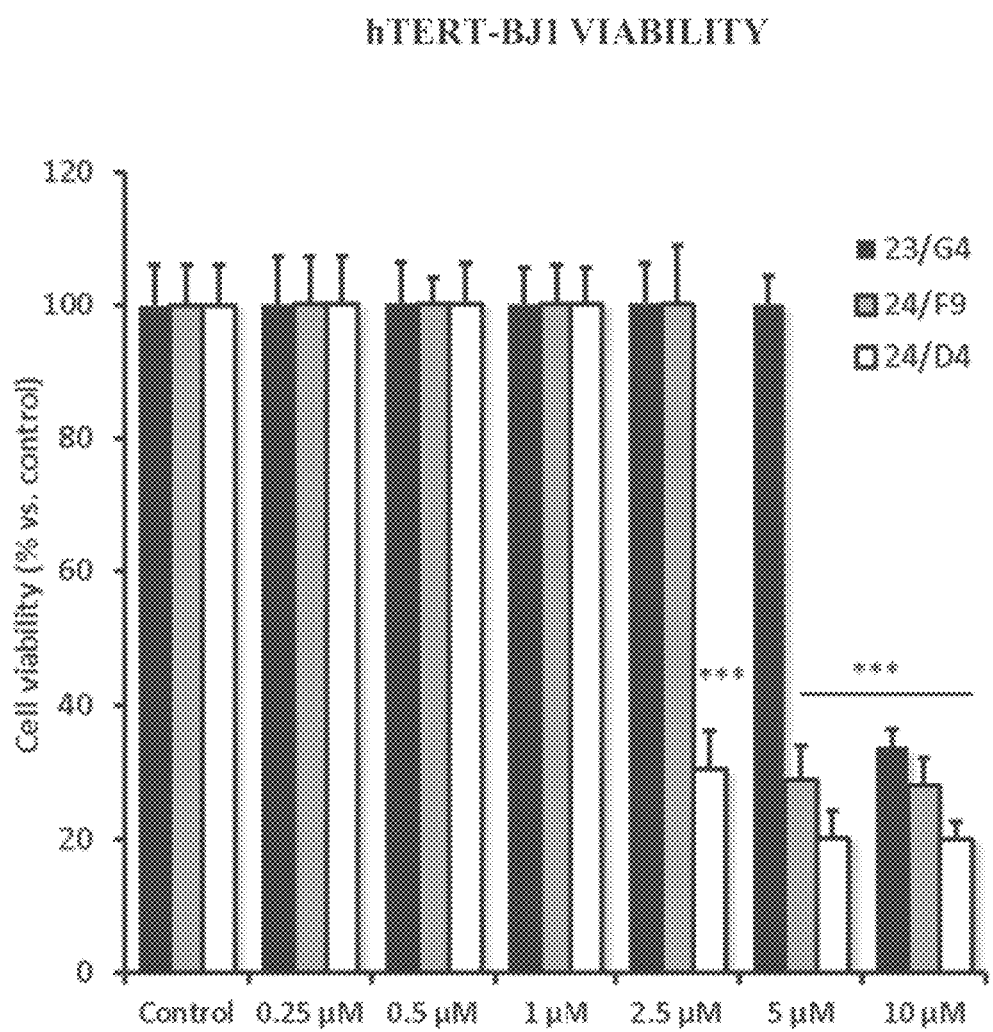
FIG. 6B shows the effects of three mitoriboscin compounds on the cell viability of hTERT-BJ1 cells.
Figure 7A:
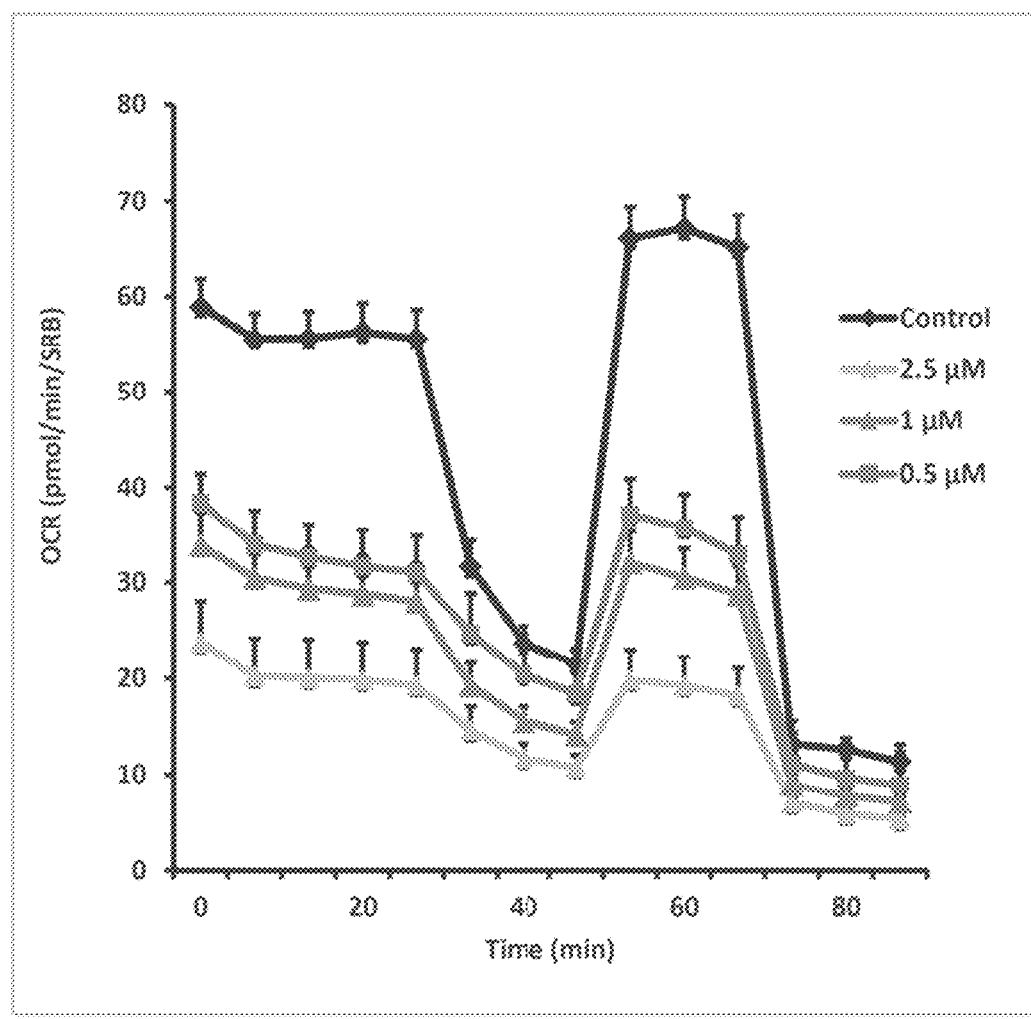
FIG. 7A shows the effects of compound 23/G4 on oxygen consumption rate (OCR) over time in MCF7 cells.
Figure 7B:
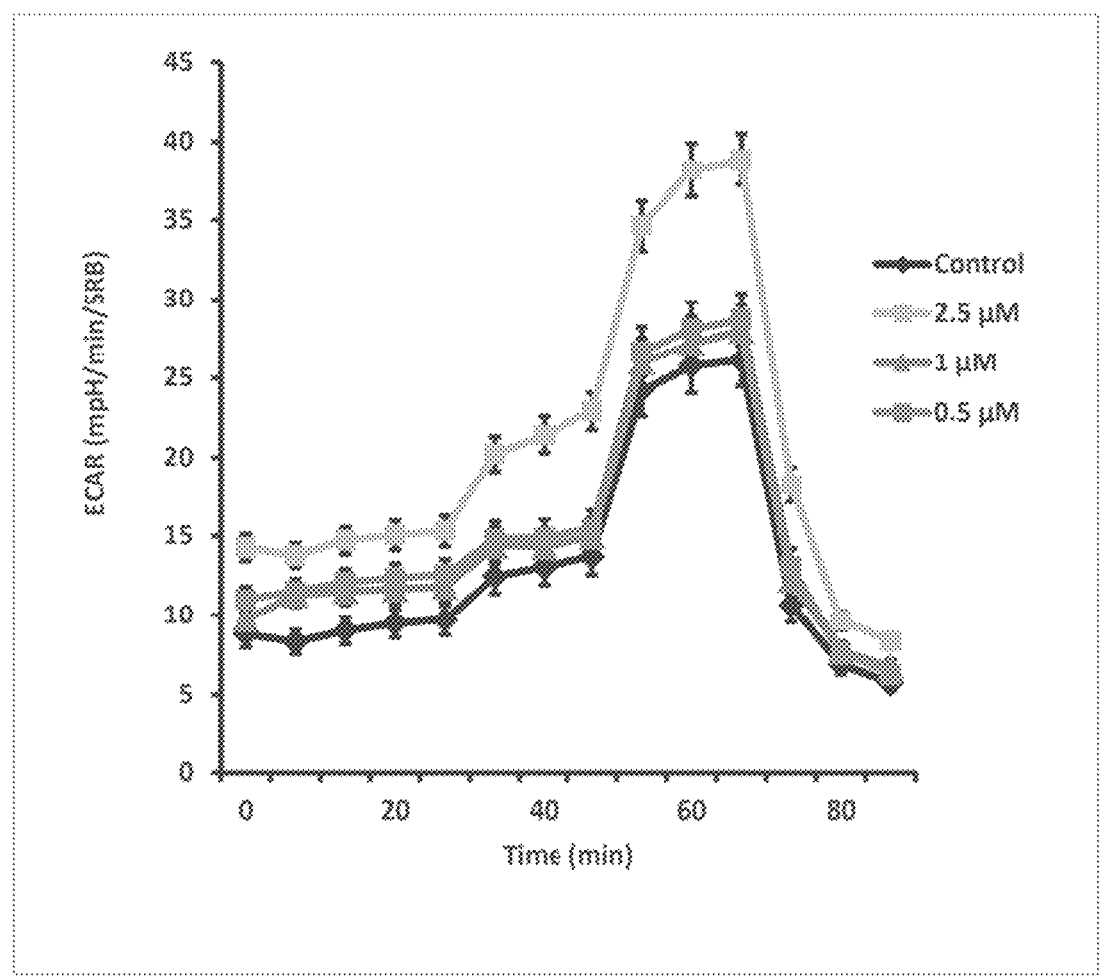
FIG. 7B shows the effects of compound 23/G4 on extracellular acidification rate (ECAR) over time in MCF7 cells.
Figure 7C:
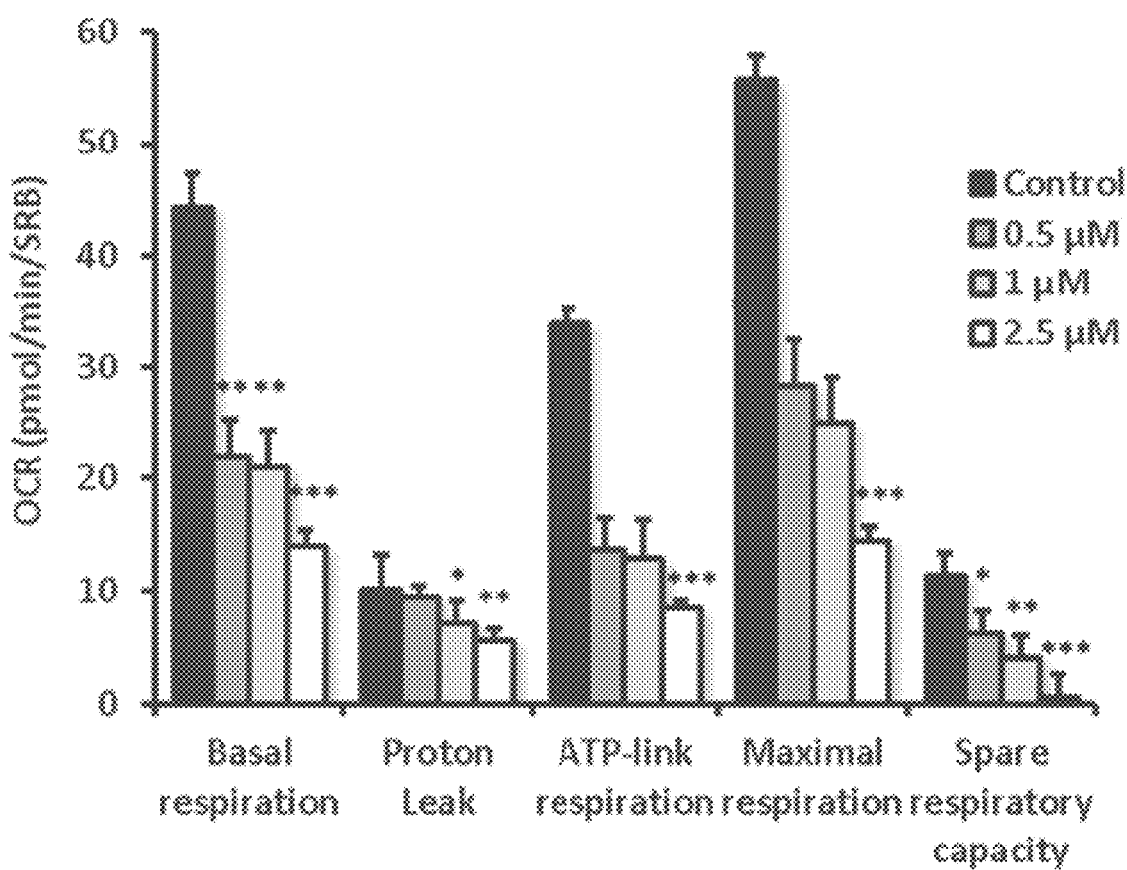
FIG. 7C shows the effects of compound 23/G4 on OCR for basal respiration, proton leak, ATP-linked respiration, maximal respiration, and spare respiratory capacity.
Figure 7D:
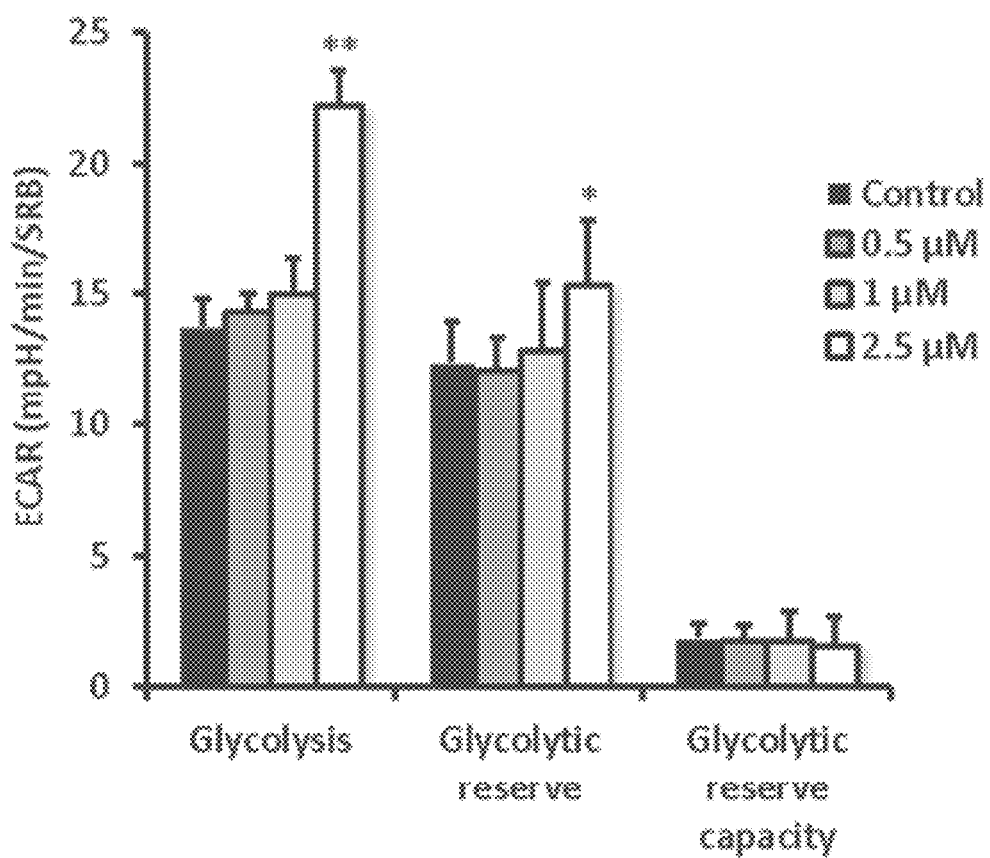
FIG. 7D shows the effects of compound 23/G4 on ECAR for glycolysis, glycolytic reserve, and glycolytic reserve capacity.
Figure 8A:
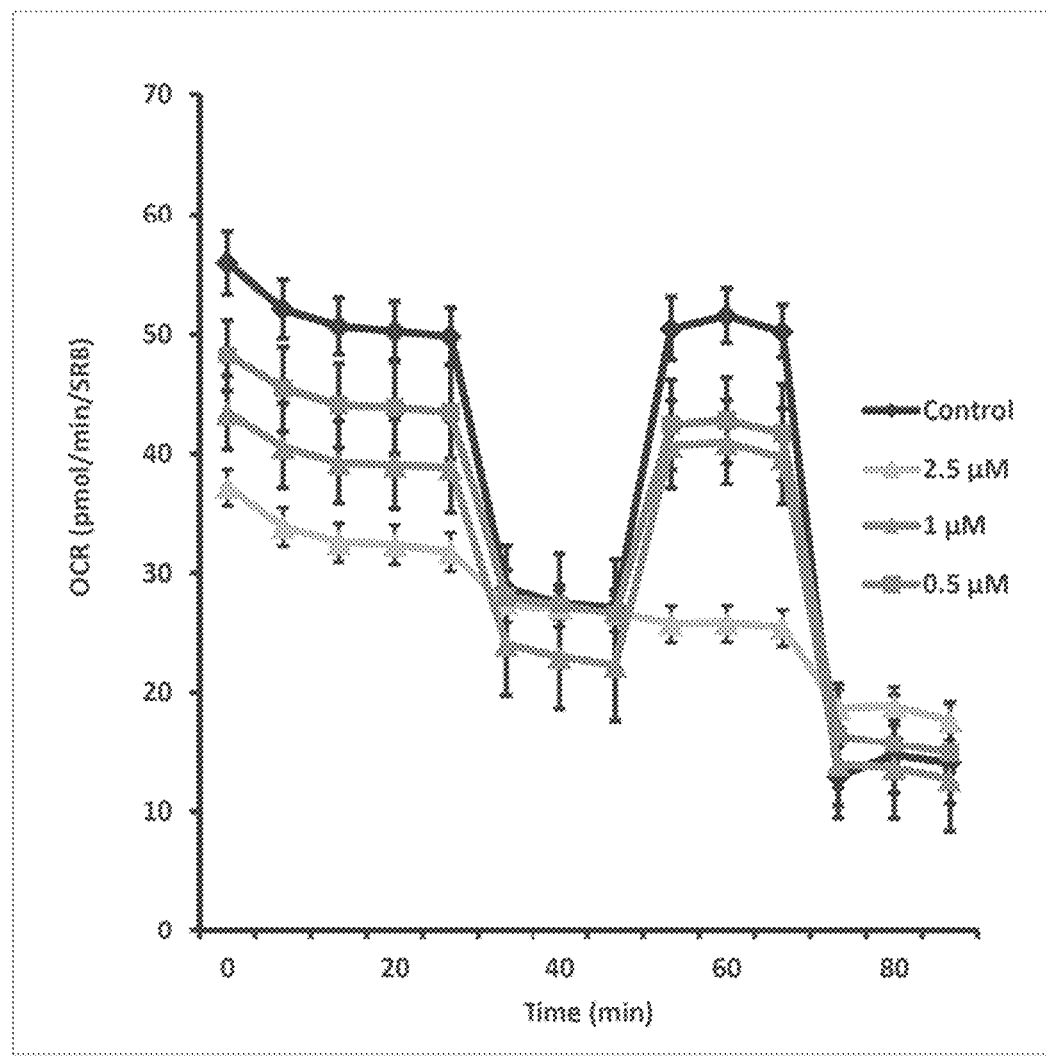
FIG. 8A shows the effects of compound 24/D4 on oxygen consumption rate (OCR) over time in MCF7 cells.
Figure 8B:
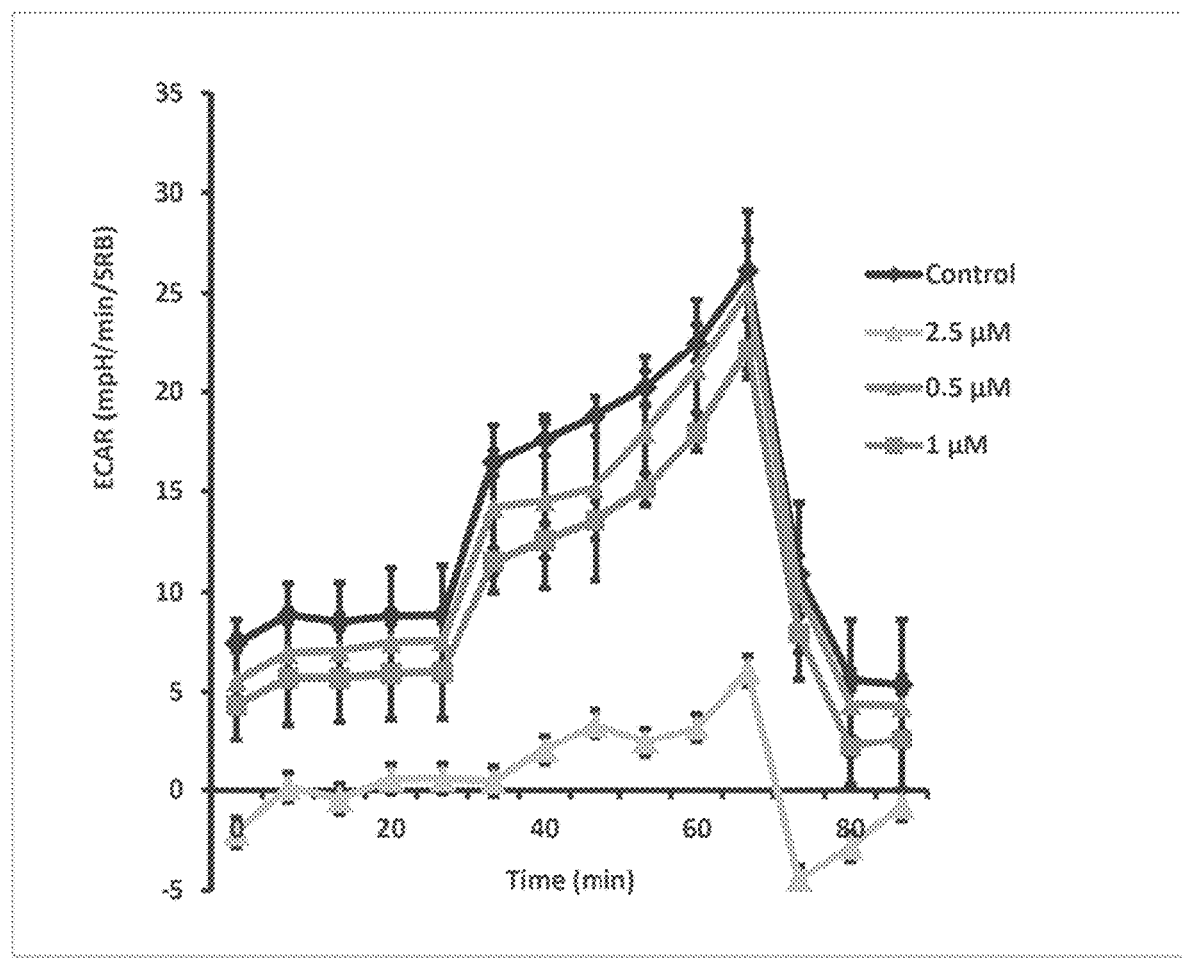
FIG. 8B shows the effects of compound 24/D4 on extracellular acidification rate (ECAR) over time in MCF7 cells.
Figure 8C:
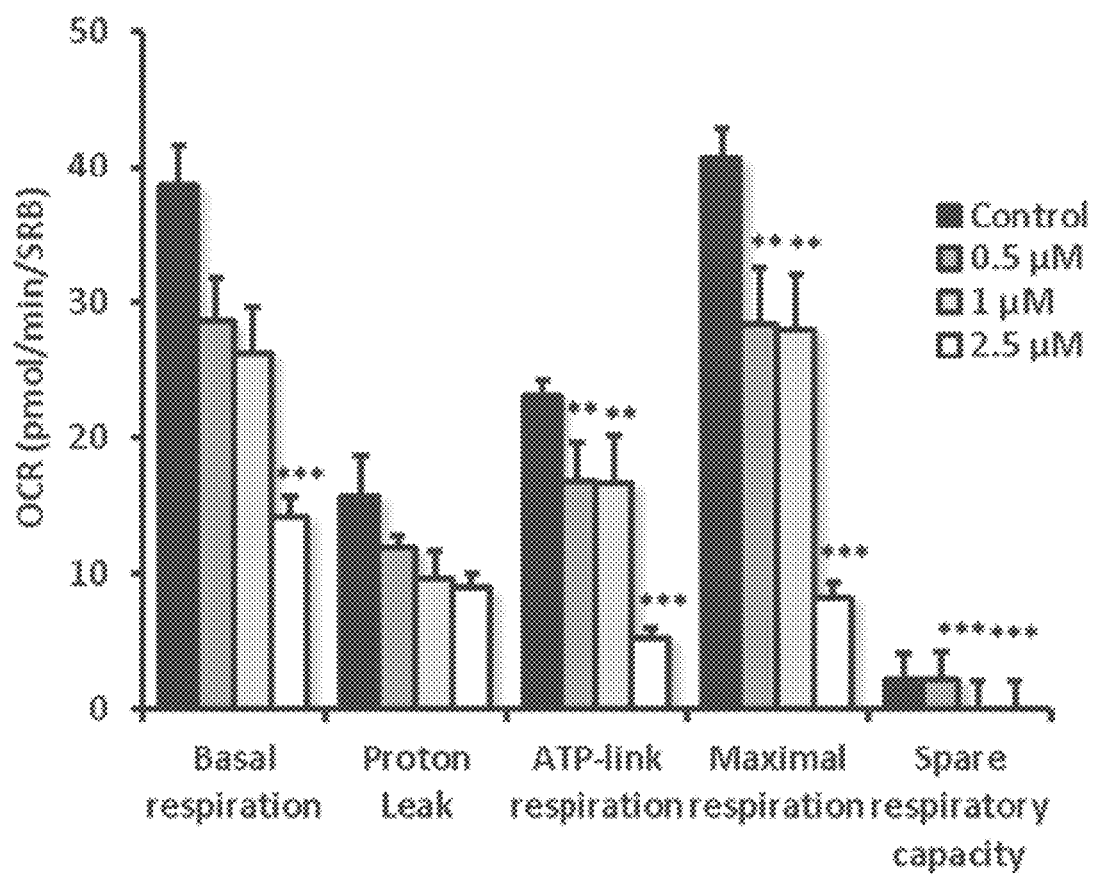
FIG. 8C shows the effects of compound 24/D4 on OCR for basal respiration, proton leak, ATP-linked respiration, maximal respiration, and spare respiratory capacity.
Figure 8D:
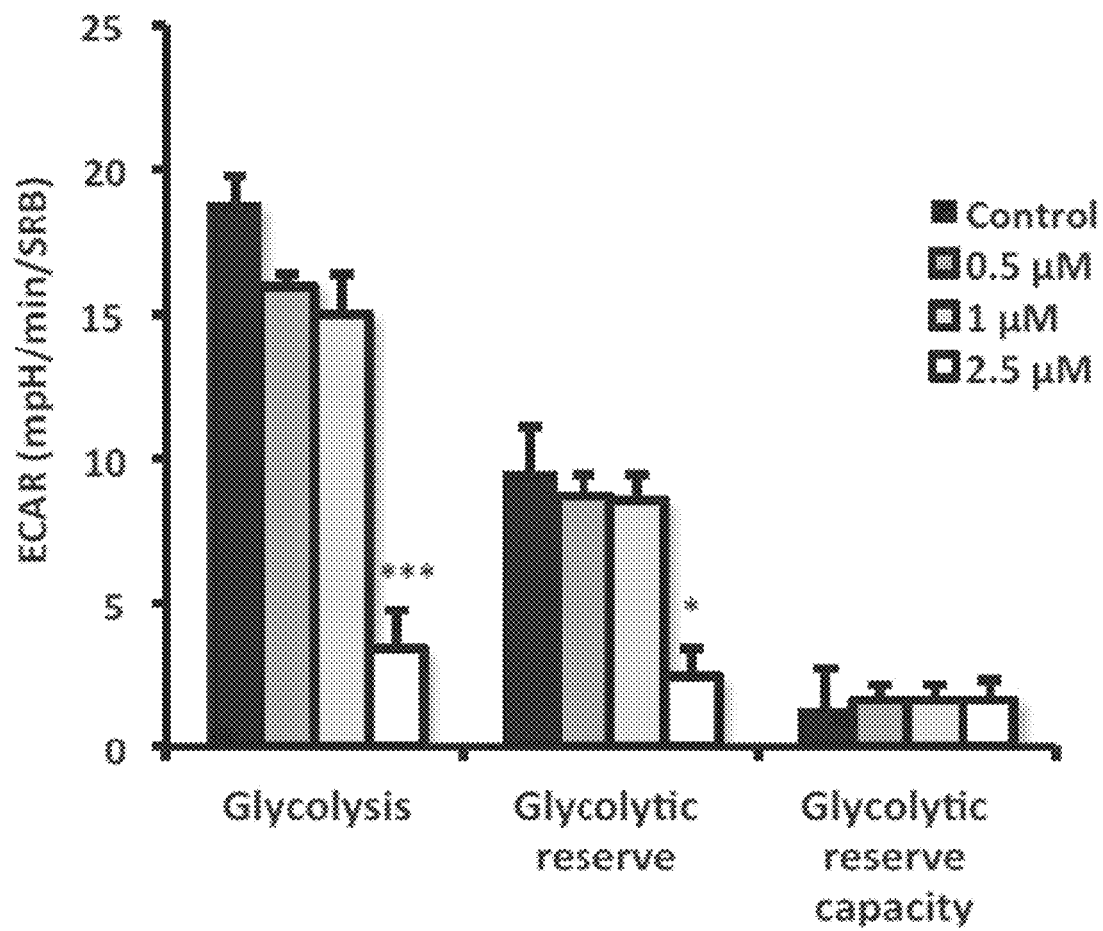
FIG. 8D shows the effects of compound 24/D4 on ECAR for glycolysis, glycolytic reserve, and glycolytic reserve capacity.
Figure 9A:
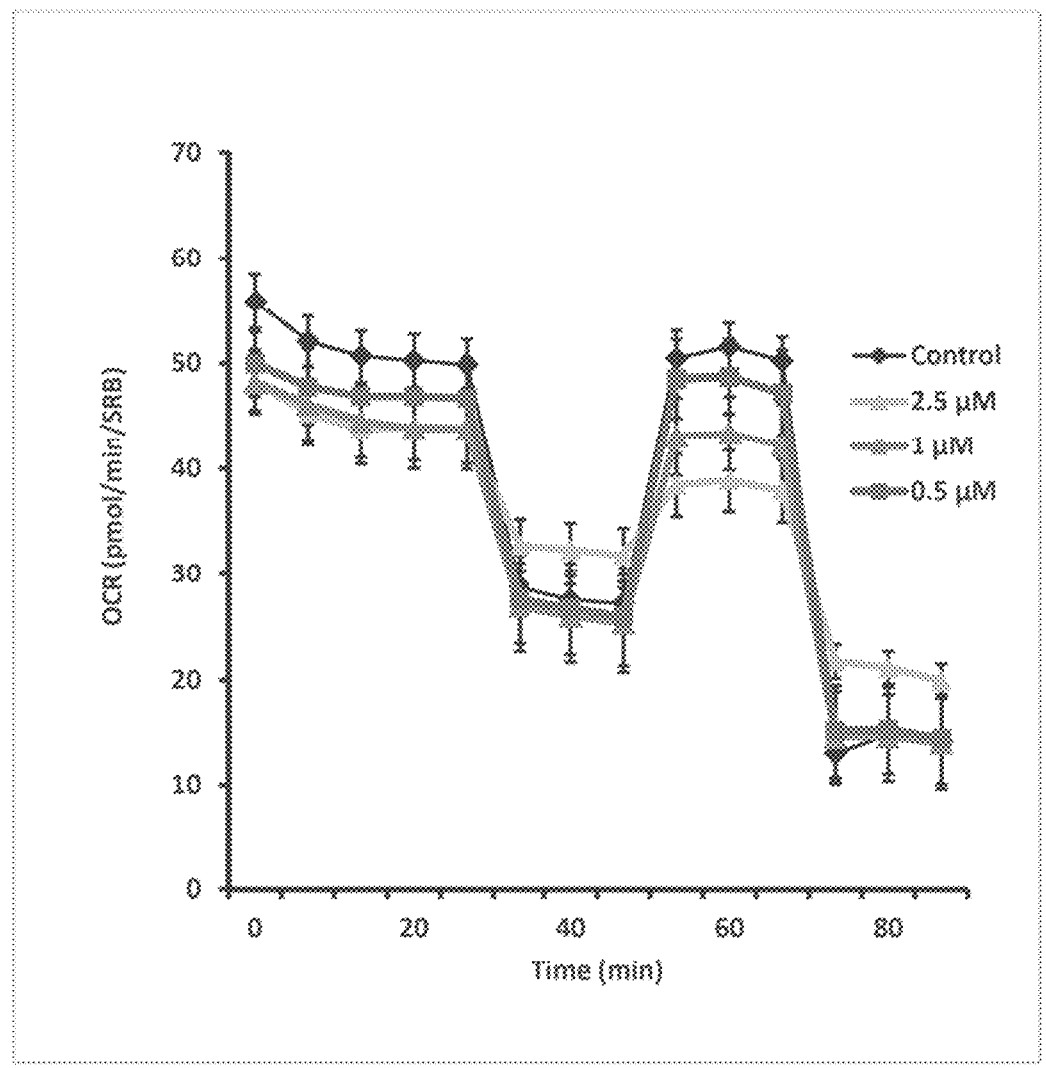
FIG. 9A shows the effects of compound 24/F9 on oxygen consumption rate (OCR) over time in MCF7 cells.
Figure 9B:
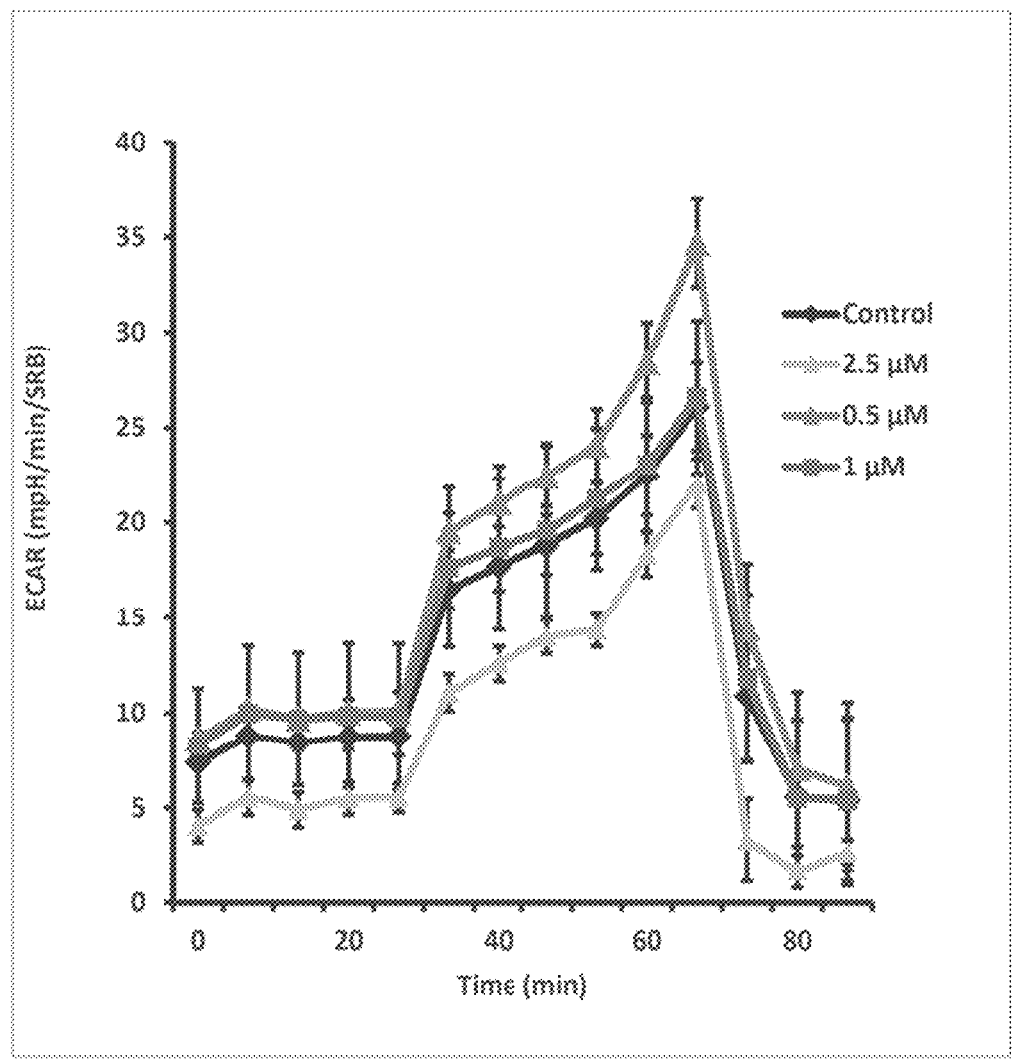
FIG. 9B shows the effects of compound 24/F9 on extracellular acidification rate (ECAR) over time in MCF7 cells.
Figure 9C:
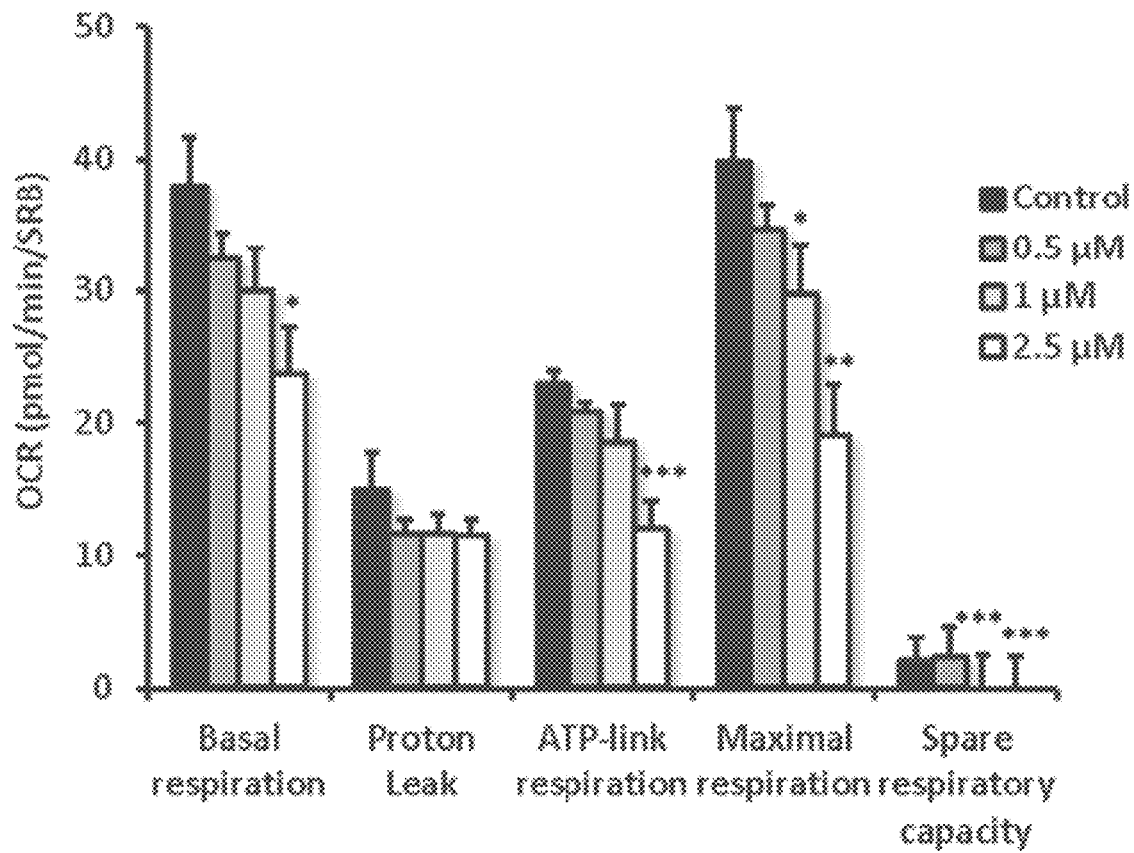
FIG. 9C shows the effects of compound 24/F9 on OCR for basal respiration, proton leak, ATP-linked respiration, maximal respiration, and spare respiratory capacity.
Figure 9D:
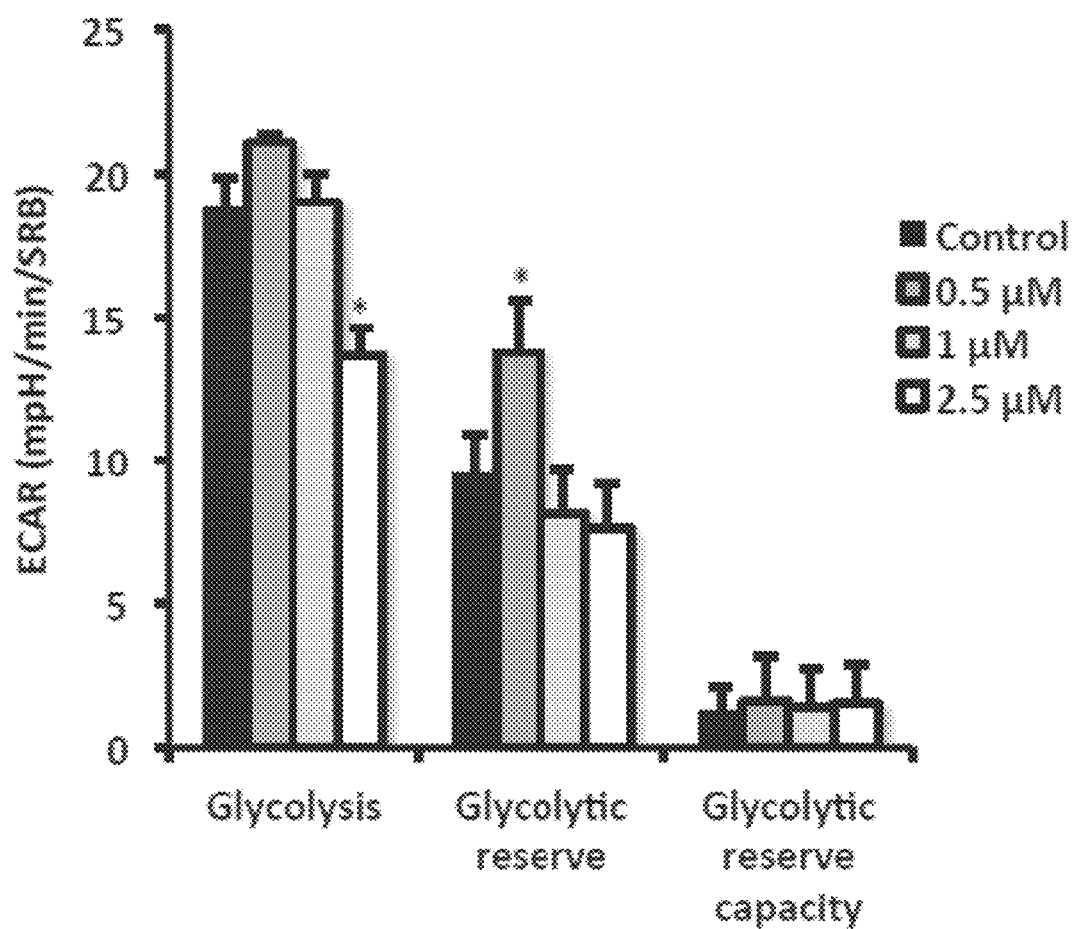
FIG. 9D shows the effects of compound 24/F9 on ECAR for glycolysis, glycolytic reserve, and glycolytic reserve capacity.

The inventors' results demonstrated that 23/G4 (Group 1), 24/F9 (Group 2) and 24/D4 (Group 3) all dose-dependently inhibited mitochondrial oxygen-consumption in MCF7 cells, with 23/G4 being the most potent (FIGS. 7, 8 and 9). 23/G4 reduced ATP levels by >50% at a concentration of only 500 nM. In addition, 23/G4 reduced ATP levels by ~75% at 2.5 µM (FIG. 7). Remarkably, treatment with 23/G4, at the same concentrations, had little or no effect on the overall cell viability of MCF7 monolayers (FIG. 6). Therefore, 23/G4 very effectively depleted ATP levels, without showing significant cytotoxicity.

Figure 10A:
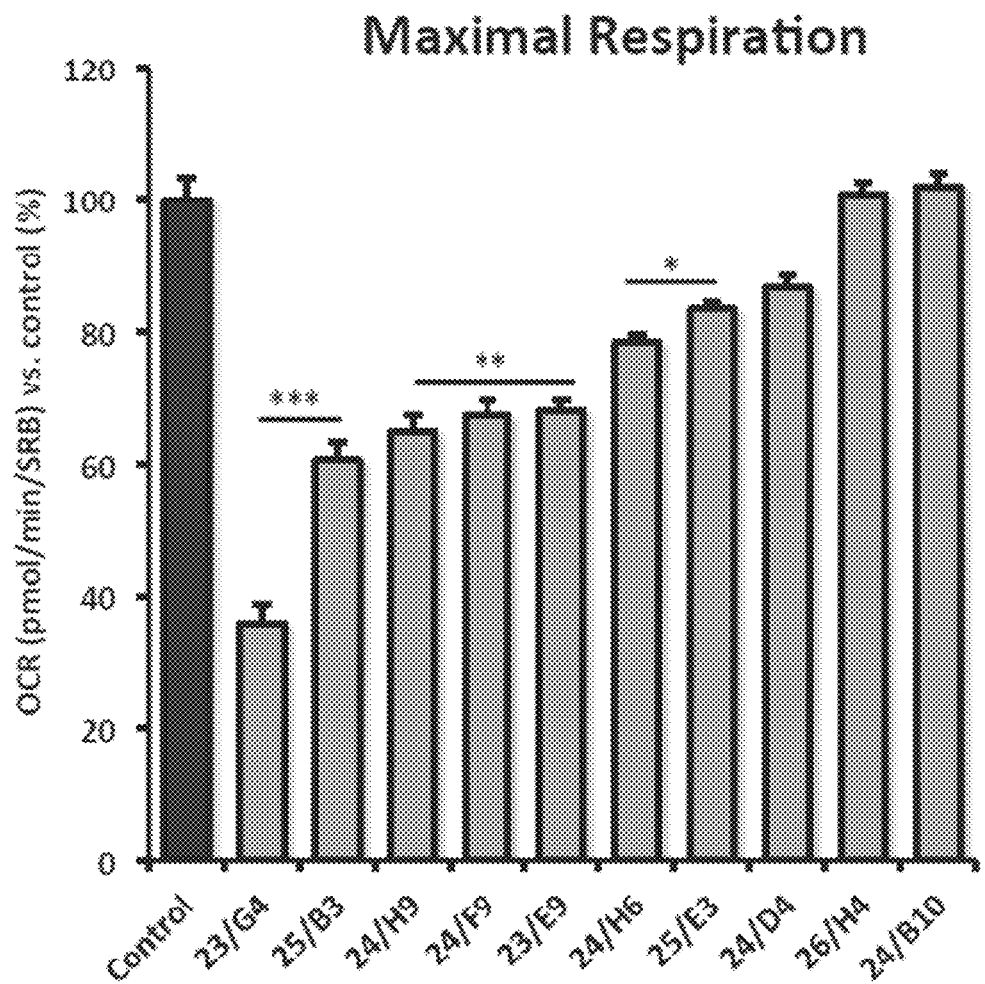
FIG. 10A shows the effects of ten mitoriboscin compounds on maximal respiration in MCF7 cells.
Figure 10B:
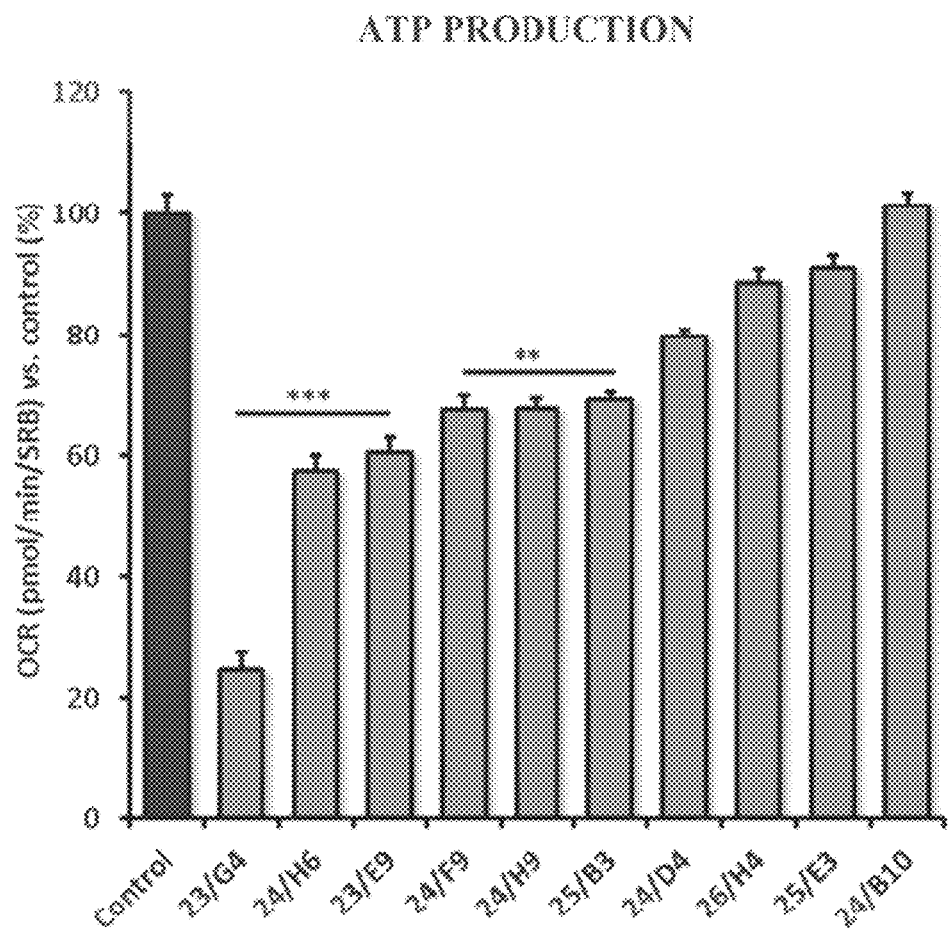
FIG. 10B shows the effects of ten mitoriboscin compounds on ATP production in MCF7 cells.

The data demonstrated that 23/G4 induced an increase in glycolysis rates by more than 1.5-fold, while 24/F9 and 24/D4 both suppressed glycolysis. This could explain why 24/F9 and 24/D4 were more potent than 23/G4 in the mammosphere assay, where 24/F9 and 24/D4 both reduced mammosphere formation by ~90% at a concentration of 5 µM (FIG. 5). The rank order potency of the top 10 hits for their ability to reduce i) maximal respiration and ii) ATP production is shown in FIG. 10. Note that the top 6 compounds in this regard were 23/G4, 25/B3, 24/H9, 24/F9, 23/E9 and 24/H6, with 23/G4 being the most potent, yielding a greater than 75% reduction in ATP levels at 5 µM.

Figure 11:
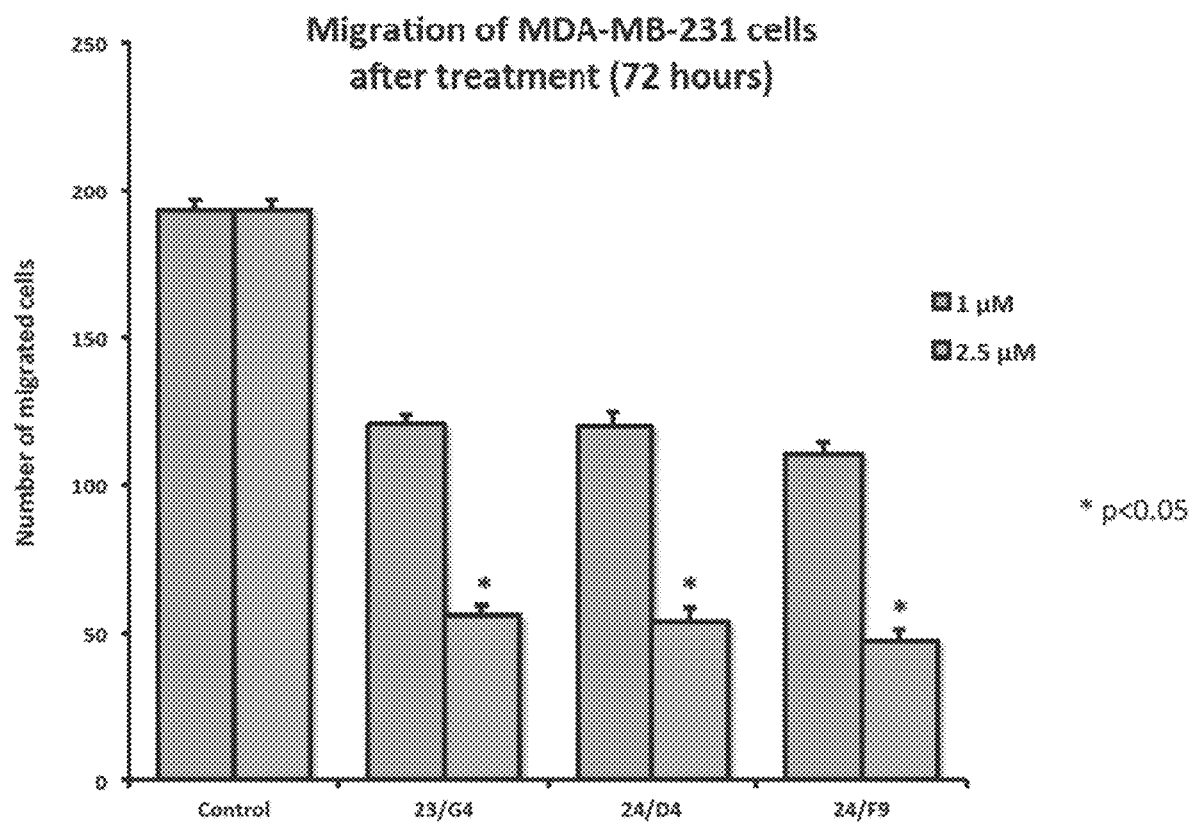
FIG. 11 shows the effects of three mitoriboscin compounds at two different concentrations on cell migration in MDA-MB-231 cells.

As EMT and cell invasion are phenotypic features associated with "stemness" and distant metastasis, the effects of these compounds on the ability of another more aggressive breast cancer cell line, MDA-MB-231, to undergo cell migration were evaluated. FIG. 11 shows that 23/G4, 24/D4 and 24/F9 all inhibited cell migration by more than 70%, at a concentration of 2.5 µM.

The present approach allows for testing compounds for anti-cancer properties by considering compound effects on mammosphere formation and cell migration. Using the methods disclosed herein, 23/G4 (Group 1) appears to be a promising new lead compound, as it is more selective at targeting CSCs and cancer cells, while sparing normal cells (FIG. 6). 23/G4 is the most potent hit compound that effectively reduces mitochondrial ATP levels and induces glycolysis. It should be appreciated that those skilled in the art may use other methods known in the art for assessing a candidate mitochondrial inhibitor's effects on a particular cell line without departing from the present approach. It should also be appreciated that those skilled in the art may assess a candidate mitochondrial inhibitor's effects on other cancer types, as the inhibitors target cancer stem cells (CSCs). CSCs show conserved features across most cancer types. Antibiotics such as doxycycline and erythromycin, which bind to mitochondrial ribosomes as an off-target effect, show efficacy in twelve different cell lines, representing eight different cancer types. These include: ductal carcinoma in situ (DCIS), breast, ovarian, pancreatic, lung carcinomas, as well as melanoma and glioblastoma.

FIG. 1 depicts the evolution of aerobic bacteria into mitochondrial organelles over millions of years of symbiosis and adaptation. In view of this evolutionary history, compounds that target mitochondrial protein translation in cancer cells may also possess anti-microbial activity. The present approach provides methods of testing compounds for anti-microbial activity, as well as novel compounds having anti-microbial activity. To demonstrate that mitochondrial inhibitors function as broad-spectrum antibiotics, the inventors tested the anti-microbial activity of the top three compounds (24/F9, 24/D4 and 23/G4) against two gram-positive bacterial strains (*Staph. aureus* and *Strep. pyogenes*) three gram-negative bacterial strains (*E. coli, P. aeruginosa, K. pneumoniae*), and the pathogenic yeast strain *C. albicans*.

The antimicrobial effects of a candidate mitochondria inhibitor may be evaluated using the Kirby-Bauer disc-diffusion method, performed according to the Clinical and Laboratory Standards Institute (CLSI) guidelines, and results are interpreted using CLSI breakpoints. Antibiotics disks against gram (+ve) and gram (−ve) bacteria (from Oxoid™) may be used as positive controls. The inventors assessed the antibiotic effects of certain mitoriboscins described herein based on the following methodology. Compounds 24/D4, 24/F9, and 23/G4 identified herein were prepared by dissolving them in dimethyl sulfoxide (DMSO, from Sigma/Aldrich Company; St. Louis, Mo., USA) and were utilized to impregnate the Blank Antimicrobial Susceptibility Disks (Oxoid™). Overnight cultures of bacteria tested were adjusted to a turbidity of 0.5 McFarland standards ($10^6$ CFU/ml) before inoculation onto agar plates with sterile cotton swabs. A cotton swab dipped in the cell culture was streaked onto an agar plate surface in such a way as to obtain a uniform layer of bacteria across the whole surface. After 10-15 minutes, the antibiotics disks or novel compounds disks were placed on the inoculated surface of the agar plates; then, all agar plates were incubated at 37° C. overnight. The diameters of inhibition were measured and susceptibility was expressed in terms of resistance (R), moderate susceptibility (I) and susceptibility (S). Agar plates inoculated with bacteria tested with impregnated DMSO disks were used as controls. The result obtained on a single bacteria strain was confirmed by Sensi test gram-positive and Sensi test-gram-negative kits (Liofilchem S.R.L.). Disc-diffusion susceptibility tests were performed in triplicate and repeated three times independently.

The minimal inhibitory concentration (MIC) of the antibacterial compounds may be determined using the broth dilution method, according to CLSI guidelines. Test compound solutions (or antibiotic solutions used as positive controls) were diluted, serially, with MHB medium. Then, the suspensions of the microorganisms, prepared from overnight cultures of bacteria in the MHB medium, at a concentration of $10^6$ CFU/ml, were added to each dilution in a 1:1 ratio. McFarland standards were used as a reference to adjust the turbidity of microorganism suspensions. Growth (or lack thereof) of the microorganisms was determined after incubation for 24 hours at 37° C. by turbidimetry (wavelength of 600 nm). MIC 50 and MIC 99 are defined as the minimum inhibitory concentration of the compound required for 50% and 99% inhibition of bacterial growth. The negative control tubes did not contain bacterial inoculum and the positive control tubes contained only DMSO. The susceptibility test by measurement of MIC was performed in triplicate and repeated three times independently. Statistical significance was determined using the Student's t-test and values of less than 0.05 were considered significant.

TABLE 1

Gram-Positive Bacterial Antibiotic Sensitivity.

| | | Susceptibility Testing Gram-positive | | | | | |
|---|---|---|---|---|---|---|---|
| | | Staph. aureus ATCC 25923 | | | Strept. pyogenes ATCC 19615 | | |
| | CONTENT | EVALUATION | | | | | |
| ANTIBIOTIC/INHIBITOR | µg | S | I | R | S | I | R |
| Ciprofloxacin | 4 | X | | | X | | |
| Rifampicin | 4 | X | | | | X | |
| 23/G4 | 8 | X | | | X | | |
| Gentamicin | 8 | X | | | X | | |
| Tobramycin | 8 | X | | | | X | |
| Levofloxacin | 8 | X | | | X | | |
| Pefloxacin | 8 | X | | | X | | |
| Azithromycin | 8 | X | | | | X | |
| Clarithromycin | 8 | X | | | | X | |
| Erythromycin | 8 | X | | | | X | |
| Miokamycin | 8 | | X | | | | X |
| Roxitromycin | 8 | X | | | | X | |
| Co-trimoxazole | 8 | X | | | X | | |
| Amoxicillin/Clavulanic acid | 8/4 | | X | | X | | |
| Piperacillin | 16 | X | | | X | | |
| 24/D4 | 32 | X | | | X | | |
| Netilmicin | 32 | X | | | X | | |
| Cefaclor | 32 | | X | | | X | |
| Cefixime | 32 | X | | | | X | |
| Cefonicid | 32 | X | | | X | | |
| Ceftazidime | 32 | X | | | X | | |
| Cefuroxime | 32 | X | | | X | | |
| Ampicillin/Sulbactam | 32/16 | | X | | X | | |
| 24/F9 | 64 | X | | | X | | |
| Ceftriaxone | 64 | X | | | X | | |
| Fosfomycin | 200 | X | | | | X | |

Table 1 summarizes gram-positive anti-bacterial activity of mitoriboscins compounds 24/F9 (Group 2), 24/D4 (Group 3), and 23/G4 (Group 1) compared to known antibiotics and across two gram-positive bacterial strains (Staph. aureus and Strep. pyogenes). The column label S identifies sensitivity, I identifies intermediate, and R identifies resistant. Tables 1 and 2 (below) illustrate how all five bacterial strains tested are sensitive to the mitoriboscin compounds 24/F9, 24/D4, and 23/G4. Similar activity is present in the other mitoriboscin compounds disclosed herein, particularly mitoribocyclines, mitoribomycins, mitoribosporins, and mitoribofloxins. No growth inhibition was seen in the control (DMSO).

TABLE 2

Gram-Negative Bacterial Antibiotic Sensitivity.

| | | Susceptibility Testing Gram-negative | | | | | | | | |
|---|---|---|---|---|---|---|---|---|---|---|
| | | *E. coli* ATCC 25922 | | | *P. auriginosa* ATCC 27853 | | | *K. pneumoniae* ATCC 13883 | | |
| ANTIBIOTIC/INHIBITOR | CONTENT μg | S | I | R | S | I | R | S | I | R |
| Ciprofloxacin | 4 | X | | | X | | | X | | |
| Rifampicin | 4 | | X | | | X | | | X | |
| Gentamicin | 8 | X | | | X | | | X | | |
| Tobramycin | 8 | | X | | X | | | X | | |
| Lomefloxacin | 8 | X | | | | X | | | X | |
| Levofloxacin | 8 | X | | | X | | | X | | |
| Pefloxacin | 8 | X | | | X | | | X | | |
| Co-trimoxazole | 8 | X | | | X | | | X | | |
| 24/D4 | 32 | X | | | X | | | X | | |
| 23/G4 | 32 | | X | | X | | | X | | |
| Amikacin | 32 | X | | | X | | | X | | |
| Ceftazidime | 32 | X | | | X | | | X | | |
| Cefuroxime | 32 | X | | | X | | | X | | |
| Nalidixic acid | 32 | | X | | X | | | X | | |
| Teicoplanin | 32 | X | | | | X | | | X | |
| Aztreonam | 32 | X | | | X | | | X | | |
| Amoxicillin/Clavulanic acid | 32/16 | | X | | X | | | X | | |
| Ampicillin/Sulbactam | 32/16 | X | | | | X | | | X | |
| Cefotaxime | 64 | X | | | X | | | X | | |
| 24/F9 | 64 | X | | | | X | | X | | |
| Cefoperazone | 64 | X | | | X | | | X | | |
| Cefotaxime | 64 | X | | | X | | | X | | |
| Ceftriaxone | 64 | X | | | X | | | X | | |
| Nitrofurantoin | 128 | X | | | X | | | X | | |
| Pipe racillin/Tazobactam | 128/4 | X | | | X | | | X | | |
| Ticarcillin/Clavulanic acid | 128/4 | X | | | X | | | X | | |
| Fosfomycin | 200 | | X | | X | | | X | | |

Table 2 summarizes the anti-bacterial activity of mitoriboscin compounds 24/F9, 24/D4 and 23/G4, compared to known antibiotics, across three different gram-negative bacterial strains (*E. coli, P. aeruginosa, K. pneumoniae*). The column label S identifies sensitivity, I identifies intermediate, and R identifies resistant.

In order to determine the minimal inhibitory concentration (MIC) for 24/F9, 24/D4 and 23/G4, the broth dilution method may be performed. Using this method, the MIC determination results demonstrated agreement with the disc-diffusion susceptibility test.

TABLE 3

Minimum Inhibitory Concentrations (MIC): Bacterial Strains and Pathogenic Yeast
Minimum inhibitory concentration (compare with common antibiotics)

| | MIC μg/ml | | | | | | | | | | | |
|---|---|---|---|---|---|---|---|---|---|---|---|---|
| | *E. coli* ATCC 25922 | | *P. auriginosa* ATCC 27853 | | *K. pneumoniae* ATCC 13883 | | *Staph. aureus* ATCC 25923 | | *Strept. pyogenes* ATCC 19615 | | *C. albicans* ATCC 13883 | |
| ANTIBIOTIC/ INHIBITOR | 50% | 99% | 50% | 99% | 50% | 99% | 50% | 99% | 50% | 99% | 50% | 99% |
| 24/D4 | 16 | 32 | 16 | 32 | 16 | 32 | 16 | 32 | 16 | 32 | — | >64 |
| 23/G4 | >16 | >32 | 16 | 32 | 16 | 32 | 4 | 8 | 4 | 8 | 8 | 16 |
| 24/F9 | 32 | 64 | >32 | >64 | 32 | 64 | 32 | 64 | 32 | 64 | — | >64 |
| DOXYCYCLINE | 0.5 | 2 | 1 | 2 | 2 | 4 | 0.5 | 1 | 0.5 | 1 | — | >64 |
| LINEZOLID | 128 | >128 | 64 | 256 | 128 | 256 | 1 | 2 | 1 | 2 | — | — |
| AMOXICILLIN | 16 | >32 | 128 | 256 | 32 | >64 | 4 | 8 | 4 | 8 | — | — |
| MICONAZOLE | — | — | — | — | — | — | — | — | — | — | 0.5 | 1 |

Table 3 shows the MIC determination results obtained as compared to known antibiotics, against the tested bacterial strains and *C. albicans*. Compound 23/G4 shows the greatest broad-spectrum activity and potency, as compared with compounds 24/F9 and 24/D4.

TABLE 4

Minimum Inhibitory Concentrations (MIC): MRSA v. MSSA
Minimum inhibitory concentration (compare with common antibiotics)

| | MIC µg/ml | | | |
|---|---|---|---|---|
| ANTIBIOTIC/ | MRSA ATCC 43300 | | MSSA ATCC 25923 | |
| INHIBITOR | 50% | 99% | 50% | 99% |
| 24/D4 | 16 | >32 | 16 | 32 |
| 23/G4 | 16 | >32 | 4 | 8 |
| 24/F9 | 64 | >64 | 32 | 64 |
| AMOXICILLIN | >64 | >64 | 4 | 8 |

Table 4 shows that Methicillin-resistant *Staphylococcus aureus* (MRSA) is also sensitive to 23/G4 and 24/D4. It was confirmed that this strain of MRSA was indeed resistant to amoxicillin, as predicted. This result shows it may be possible to use this new drug discovery strategy employing human cancer cells to isolate new antibiotics that can target drug-resistant bacteria, such as MRSA.

The data demonstrates that the mitoriboscins identified by the present approach have anti-cancer, anti-bacterial properties, and are suitable for pharmaceutical compositions.

The inventors have shown that compounds inducing acute ATP depletion in cancer cells can sensitize those cells to radiation, ultraviolet light, chemotherapeutic agents, natural substances, and/or caloric restriction. Mitoriboscins, as discussed herein, have demonstrated ATP-depletion effects. Based on these preliminary results, mitoriboscins may also be used as radiosensitizers and/or photo-sensitizers. Use as radiosensitizers and/or photo-sensitizers may be in combination with other treatment vectors, including but not limited to other cancer treatment methods as may be known in the art, and cancer treatment through inhibiting mitochondrial biogenesis as disclosed herein. Similarly, mitoriboscins may be used to functionally sensitize bulk cancer cells and cancer stem cells to chemotherapeutic agents, pharmaceuticals, and/or other natural substances, such as dietary supplements and caloric restriction.

In addition to anti-cancer and anti-biotic behavior, the mitochondrial inhibitors that can be identified by the present approach have the potential to slow the mammalian aging process. Genetic inhibition of mitochondrial protein translation has been shown to have beneficial side-effects, and in particular the side effect of slowing of the aging process and increased lifespan in model organisms. Lower steady-state levels of Mrps5 (a mitoribosomal protein) is strongly functionally correlated with longer murine lifespan, resulting in a significant increase of ~250 days. In addition, selective knock-down of Mrps5 in *C. elegans* dramatically increases lifespan. Mrps5 knock-down worms show significant decreases in mitochondrial respiration and ATP production. Similarly, knock-down of the worm homologs of mitochondrial complex I, III, IV and V, as well as several TCA cycle enzymes, all robustly extended lifespan, further implicating reduced OXPHOS activity and lower ATP levels as the mechanism. Finally, pharmacological inhibition of mitochondrial biogenesis (using the off-target effects of doxycycline), also significantly increases lifespan in *C. elegans*. Thus, lower doses of the mitoriboscins may be used to therapeutically target the aging process and to extend lifespan.

Mitoriboscins may also be used to reverse drug resistance in cancer cells. Drug resistance is thought to be based, at least in part, on increased mitochondrial function in cancer cells. In particular, cancer cells demonstrating resistance to endocrine therapies, such as tamoxifen, are expected to have increased mitochondrial function. Mitoriboscins inhibit mitochondrial function, and therefore may be useful in reducing and, in some cases reversing, drug resistance in cancer cells.

Mitoriboscins may also be used as male contraceptives and/or as spermistatic or sperm-immobilizing agents. The human sperm cell consists of a head and a flagellum. The flagellum includes a neck, middle piece, and tail. The middle piece typically has 10-14 spirals of mitochondria surrounding the axial filament in the cytoplasm. These mitochondria provide motility to the sperm and thus are often referred to as the "powerhouse of the sperm." Mitoriboscins inhibit mitochondrial function and therefore may be useful in immobilizing sperm cells to prevent conception.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measureable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A compound of the formula:

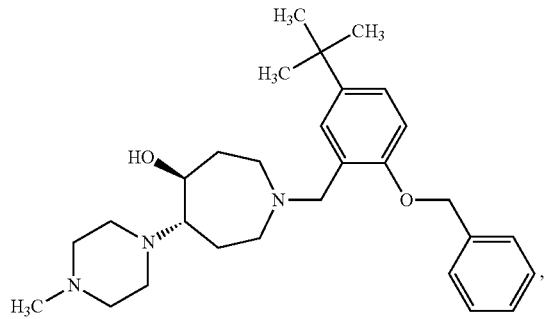 [SMILES: CN1CCN([C@H]2CCN(Cc3cc(C(C)(C)C)ccc3OCc3ccccc3)CC[C@@H]2O)CC1]

or a pharmaceutically acceptable salt thereof.

2. A method of treating cancer comprising administering to a cancer patient a pharmaceutically effective amount of a mitoriboscin compound and a pharmaceutically acceptable carrier, the mitoriboscin compound of the formula:

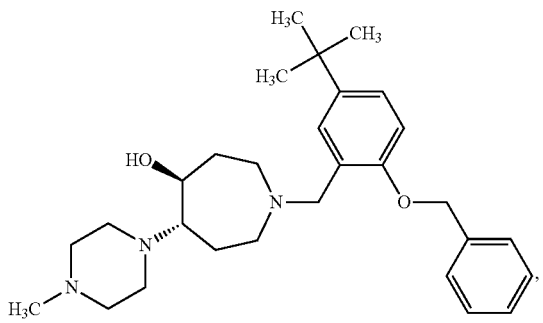 [SMILES: CN1CCN([C@H]2CCN(Cc3cc(C(C)(C)C)ccc3OCc3ccccc3)CC[C@@H]2O)CC1]

or a pharmaceutically acceptable salt thereof.

3. A method of treating a microbial infection comprising administering to a patient having a microbial infection a pharmaceutically effective amount of a mitoriboscin compound and a pharmaceutically acceptable carrier, the mitoriboscin compound of the formula:

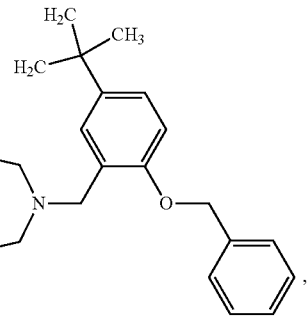

or a pharmaceutically acceptable salt thereof.

* * * * *